(12) United States Patent
Jung et al.

(10) Patent No.: US 10,300,241 B2
(45) Date of Patent: May 28, 2019

(54) METHOD AND APPARATUS FOR CONTROLLING TEMPERATURE ADJUSTMENT DEVICE

(71) Applicant: Samsung Electronics Co., Ltd., Suwon-si, Gyeonggi-do (KR)

(72) Inventors: Hyunki Jung, Seoul (KR); Sungmok Seo, Suwon-si (KR); Soonhyung Gwon, Seongnam-si (KR); Dusan Baek, Seoul (KR); Gyeyoung Lee, Seoul (KR); Sooyoung Lee, Suwon-si (KR); Junho Koh, Suwon-si (KR); Jinsung Kim, Seoul (KR); Changhyun Lee, Suwon-si (KR); Yonghyun Lim, Suwon-si (KR); Haein Chun, Suwon-si (KR)

(73) Assignee: Samsung Electronics Co., Ltd., Suwon-si (KR)

(*) Notice: Subject to any disclaimer, the term of this patent is extended or adjusted under 35 U.S.C. 154(b) by 393 days.

(21) Appl. No.: 15/180,740

(22) Filed: Jun. 13, 2016

(65) Prior Publication Data

US 2016/0361515 A1     Dec. 15, 2016

(30) Foreign Application Priority Data

Jun. 11, 2015  (KR) .................. 10-2015-0082440

(51) Int. Cl.
*A61M 21/02* (2006.01)
*A61B 5/00* (2006.01)
(Continued)

(52) U.S. Cl.
CPC .......... *A61M 21/02* (2013.01); *A61B 5/02055* (2013.01); *A61B 5/4812* (2013.01); *A61B 5/4815* (2013.01); *A61B 3/113* (2013.01);
*A61B 5/02405* (2013.01); *A61B 5/0402* (2013.01); *A61B 5/0476* (2013.01); *A61B 5/08* (2013.01); *A61B 5/11* (2013.01); *A61B 5/14532* (2013.01); *A61B 5/6892* (2013.01); *A61M 2021/0066* (2013.01); *A61M 2021/0083* (2013.01); *A61M 2205/3303* (2013.01); *A61M 2205/3368* (2013.01); *A61M 2205/3553* (2013.01);
(Continued)

(58) Field of Classification Search
CPC ... A61M 21/00; A61M 21/02; A61B 5/02055; A61B 5/4812; A61B 5/4815
USPC .................................................... 600/26–28
See application file for complete search history.

(56) References Cited

U.S. PATENT DOCUMENTS

| 2005/0143617 A1 | 6/2005 | Auphan |
| 2006/0106275 A1 | 5/2006 | Raniere |

(Continued)

FOREIGN PATENT DOCUMENTS

| JP | 2014-042773 A | 3/2014 |
| KR | 10-0791371 B1 | 1/2008 |

(Continued)

*Primary Examiner* — John P Lacyk
(74) *Attorney, Agent, or Firm* — Jefferson IP Law, LLP

(57) ABSTRACT

A method and an apparatus for controlling a temperature adjustment device using a sensing device are provided. The method includes setting a test temperature, transmitting a temperature adjustment instruction corresponding to the test temperature to a temperature adjustment device, calculating a sleep score based on bio information received from the sensor, when applying the test temperature, and determining a sleep optimal temperature based on the calculated sleep score.

16 Claims, 25 Drawing Sheets

(51) Int. Cl.
   *A61B 5/0205*   (2006.01)
   *A61B 3/113*    (2006.01)
   *A61M 21/00*    (2006.01)
   *A61B 5/024*    (2006.01)
   *A61B 5/0402*   (2006.01)
   *A61B 5/0476*   (2006.01)
   *A61B 5/08*     (2006.01)
   *A61B 5/11*     (2006.01)
   *A61B 5/145*    (2006.01)

(52) U.S. Cl.
   CPC . *A61M 2205/3592* (2013.01); *A61M 2205/50* (2013.01); *A61M 2230/06* (2013.01); *A61M 2230/10* (2013.01); *A61M 2230/18* (2013.01); *A61M 2230/201* (2013.01); *A61M 2230/40* (2013.01); *A61M 2230/50* (2013.01); *A61M 2230/63* (2013.01)

(56) References Cited

U.S. PATENT DOCUMENTS

| | | |
|---|---|---|
| 2006/0142968 A1 | 6/2006 | Han et al. |
| 2007/0083079 A1 | 4/2007 | Lee et al. |
| 2009/0121826 A1 | 5/2009 | Song et al. |
| 2010/0041966 A1 | 2/2010 | Kang et al. |
| 2011/0010014 A1 | 1/2011 | Oexman et al. |
| 2013/0002435 A1 | 1/2013 | Utter, II |
| 2013/0234823 A1 | 9/2013 | Kahn et al. |
| 2015/0150498 A1 | 6/2015 | George et al. |

FOREIGN PATENT DOCUMENTS

| | | |
|---|---|---|
| WO | 2005/055802 A2 | 6/2005 |
| WO | 2009/108228 A1 | 9/2009 |

METHOD AND APPARATUS FOR CONTROLLING TEMPERATURE ADJUSTMENT DEVICE

CROSS-REFERENCE TO RELATED APPLICATION(S)

This application claims the benefit under 35 U.S.C. § 119(a) of a Korean patent application filed on Jun. 11, 2015 in the Korean Intellectual Property Office and assigned Serial No. 10-2015-0082440, the entire disclosure of which is hereby incorporated by reference.

TECHNICAL FIELD

The present disclosure relates to a device and method for adjusting a temperature. More particularly, the present disclosure relates to a method and apparatus for controlling a temperature adjustment device using a sensing device.

BACKGROUND

The internet has been innovated from a human-based connection network in which a human generates and consumes information to an internet of things (IoT) network that gives, receives and processes information to and from distributed constituent elements such as things. Big data processing technology for connection to a cloud server and internet of everything (IoE) technology combined with IoT technology have recently appeared. In order to implement IoT, technology elements such as sensing technology, wired and wireless communication and network infrastructure, service interface technology, and security technology are required, and thus nowadays, technology of a sensor network, machine to machine (M2M), and machine type communication (MTC) for connection between things has been researched.

In an IoT environment, an intelligent internet technology (IT) service that collects and analyzes data generated in connected things to provide a new value to a life of a human may be provided. IoT may be applied to a field of a smart home, a smart building, a smart city, a smart car or a connected car, a smart grid, health care, smart home appliances, and high-tech medical service through fusion and complex between existing IT technology and various industries.

Nowadays, for a comfortable sleep environment, a method of adjusting a temperature using an air-conditioner has been used.

FIG. 1 is a diagram illustrating a method of controlling sleep using an air-conditioner according to the related art.

Referring to FIG. 1, an existing good sleep mode installed in an air-conditioner operates using a sleep information statistical value and a user's input information. In this case, the sleep information statistical value uses general statistical information of many and unspecified persons instead of a statistical value of individual users using an air-conditioner. User input information means an input of an operation time and operation temperature of an air-conditioner according to a user input.

In FIG. 1, a sleep stage may be divided into a stage 1 between a time point 111 and a time point 113, a stage 2 between the time point 113 and a time point 115, and a stage 3 between the time point 115 and a time point 117 on a time basis. The stage 1 is a segment that attempts hypnagogue. In an existing good sleep mode using an air-conditioner, when attempting hypnagogue (time point 111), a user sets a good sleep mode or previously sets a hypnagogue estimation time (segments 111-113).

In the graph of FIG. 1, a vertical axis represents a temperature, and a horizontal axis represents a time. In the graph, 130 represents a temperature change curve according to operation of an existing air-conditioner and 140 represents an appropriate peripheral temperature according to a sleep state.

Referring to the curve 130 of the graph, an existing air-conditioner slowly lowers a temperature by operating when attempting hypnagogue (time point 111), slowly raises a temperature from the time point 113, when a preset time has elapsed, and slowly raises a temperature to a wake-up scheduled time. That is, the air-conditioner operates to lower an indoor temperature in the stage 1 and to raise an indoor temperature in the stages 2 and 3.

Because such an existing good sleep control using an air-conditioner operates based on information previously input by a user or statistical information unrelated to an actual user, the good sleep control cannot reflect an actual user's sleep state.

The above information is presented as background information only to assist with an understanding of the present disclosure. No determination has been made, and no assertion is made, as to whether any of the above might be applicable as prior art with regard to the present disclosure.

SUMMARY

Aspects of the present disclosure are to address at least the above-mentioned problems and/or disadvantages and to provide at least the advantages described below. Accordingly, an aspect of the present disclosure is to provide a device and method for adjusting a temperature.

Another aspect of the present disclosure is to provide a method and apparatus for controlling a temperature adjustment device based on a sensing device for a comfortable sleep environment.

In accordance with an aspect of the present disclosure, a method of controlling an electronic device for receiving bio information from a sensor is provided. The method includes setting a test temperature, transmitting a temperature adjustment instruction corresponding to the test temperature to a temperature adjustment device, calculating a sleep score based on bio information received from the sensor when applying the test temperature, and determining a sleep optimal temperature based on the calculated sleep score.

In accordance with another aspect of the present disclosure, an electronic device for receiving bio information from a sensor is provided. The electronic device includes a transceiver configured to transmit and receive the bio information and a temperature control instruction and a controller configured to set a test temperature, to transmit a temperature adjustment instruction corresponding to the test temperature to a temperature adjustment device, to calculate a sleep score based on the bio information received from the sensor, when applying the test temperature, and to determine a sleep optimal temperature based on the calculated sleep score.

In accordance with another aspect of the present disclosure, a method of determining a sleep optimal temperature of an electronic device for receiving bio information from a sensor is provided. The method includes transmitting a temperature adjustment instruction corresponding to a first test temperature to a temperature adjustment device, receiving first bio information measured by the sensor when applying the first test temperature, calculating a first sleep score based on the received first bio information, transmitting a temperature adjustment instruction corresponding to a second test temperature to the temperature adjustment device, receiving second bio information measured by the sensor when applying the second test temperature, calculating a second sleep score based on the received second bio information, and comparing the first sleep score and the second sleep score to determine a sleep optimal temperature.

In accordance with another aspect of the present disclosure, an electronic device for receiving bio information from a sensor is provided. The electronic device includes a transceiver configured to transmit and receive the bio information and a temperature control instruction and a controller configured to transmit a temperature adjustment instruction corresponding to a first test temperature to a temperature adjustment device, to receive first bio information measured by the sensor when applying the first test temperature, to calculate a first sleep score based on the received first bio information, to transmit a temperature adjustment instruction corresponding to a second test temperature to the temperature adjustment device, to receive second bio information measured by the sensor when applying the second test temperature, to calculate a second sleep score based on the received second bio information, and to compare the first sleep score and the second sleep score to determine a sleep optimal temperature.

Other aspects, advantages, and salient features of the disclosure will become apparent to those skilled in the art from the following detailed description, which, taken in conjunction with the annexed drawings, discloses various embodiments of the present disclosure.

BRIEF DESCRIPTION OF THE DRAWINGS

The above and other aspects, features, and advantages of certain embodiments of the present disclosure will be more apparent from the following description taken in conjunction with the accompanying drawings, in which.

Throughout the drawings, it should be noted that like reference numbers are used to depict the same or similar elements, features, and structures.

DETAILED DESCRIPTION

Figure 1:
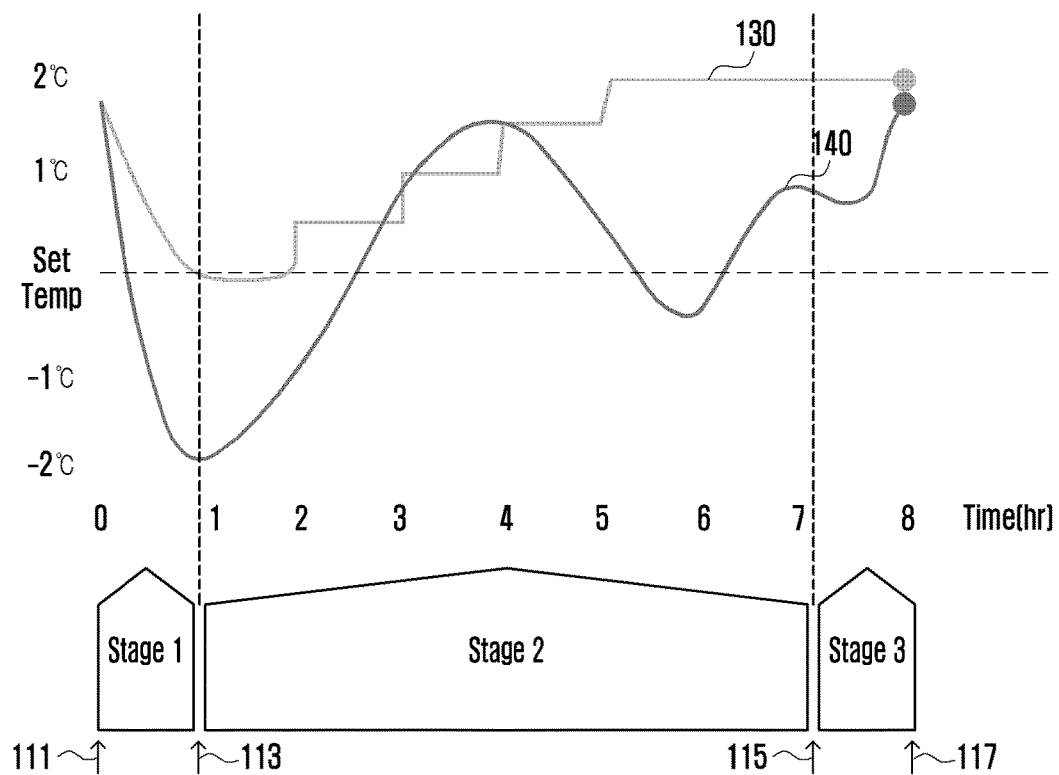
FIG. 1 is a diagram illustrating a method of controlling sleep using an air-conditioner according to the related art.

The following description with reference to the accompanying drawings is provided to assist in a comprehensive understanding of various embodiments of the present disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the present disclosure. Accordingly, it should be apparent to those skilled in the art that the following description of various embodiments of the present disclosure is provided for illustration purpose only and not for the purpose of limiting the present disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

In an embodiment of the present disclosure, a temperature adjustment device includes an air conditioning and heating device and may include various electronic devices using for adjusting a temperature. For example, a temperature adjustment device may include an air-conditioner, an electric fan, an air cleaner, a cooling mat, a heating mat, a boiler, a stove, and a heater. In an embodiment of the present disclosure, an air-conditioner is presented as an example of a temperature adjustment device or air conditioning and heating device. However, the present disclosure is not limited thereto and may be applied to operation of various electronic devices having a temperature adjustment function.

In an embodiment of the present disclosure, as an apparatus for controlling a temperature adjustment device, a gateway or an electronic device may be used. Further, the electronic device may be a gateway or a terminal for controlling home appliances. The gateway may be a smart home gateway. The smart home gateway may include a temperature adjustment device and may be a gateway for controlling home appliances. As a term used in this specification, a terminal may indicate a cellular phone, a mobile station (MS) having a wireless communication function, a user equipment (UE), a user terminal (UT), a wireless terminal, an access terminal (AT), a terminal, a subscriber unit, a subscriber station (SS), a wireless device, a wireless communication device, a wireless transmit/receive unit (WTRU), a moving node, or a mobile device. Various embodiments of the terminal may include a cellular phone, a smart phone having a wireless communication function, a wearable device, a personal digital assistant (PDA) having a wireless communication function, a wireless modem, a portable computer having a wireless communication function, a photographing device such as a digital camera having a wireless communication function, a gaming device having a wireless communication function, music storage and reproduction home appliances having a wireless communication function, internet home appliances in which wireless Internet access and browsing are available, and a mobile unit or terminal that integrates combinations of such functions.

In an embodiment of the present disclosure, a sensor may detect a user's bio signal (bio information). The bio information may be at least one of a user's blood sugar information, body temperature information, pulse information, respiration information, heartbeat information, electrocardiogram information, brainwave information, eye movement information (movement of eyeball, blink, the number of blink, movement of eyelid, and tear), and movement information. Further, the sensor may additionally detect information about a sleep stage and a sleep stage duration time. The sensor may include at least one of a sleep detection sensor, a brainwave sensor, a piezoelectric sensor, a temperature detection sensor, a movement detection sensor, a bio sensor, an optical detection sensor, a gyro sensor, and an inertia sensor.

In an embodiment of the present disclosure, a temperature control instruction may include information, a message, and a signal transmitted from an electronic device to a temperature adjustment device in order to operate the temperature adjustment device at a specific temperature. Further, the temperature control instruction may include information, a message, and a signal transmitted from an electronic device to a temperature adjustment device in order to turn on/off the temperature adjustment device.

In an embodiment of the present disclosure, sleep state related information may include information about a sleep state such as a stage of attempting hypnagogue, a hypnagogue stage, a sleep stage, an awakening, tossing and turning, and movement and information about a good sleep index, a sleep disturbance index, a hypnagogue index, a sleep index, a wake-up index, a sleep arriving time, a total sleep time, an actual wake-up time after awakening, a sleep attempt start time, a sleep start time, an awakening start time, a wake-up time, a sleep configuration score, and a sleep stage immediately before awakening.

In an embodiment of the present disclosure, sleep information may include at least one of information about a sleep score, a sleep optimal temperature, and temperature sensitivity (individual temperature sensitivity). The sleep score may be determined based on bio information or sleep state related information. Further, a method of acquiring a sleep score is not limited to the foregoing method, and a sleep score may be acquired by combining various sleep state related information suggested in an embodiment of the present disclosure. The sleep score may be displayed with various methods. The sleep score may be displayed with numerals. In an embodiment of the present disclosure, the sleep score is not limited to numerals and may be expressed with various methods such as a character, an alphabet, a percent, a symbol, a color, etc.

In an embodiment of the present disclosure, a sleep optimal temperature is determined based on bio information or sleep information. The sleep optimal temperature is specified to a user who collects bio information. A temperature having a highest sleep score among sleep scores acquired based on a test temperature may be determined as a sleep optimal temperature.

In an embodiment of the present disclosure, the sleep stage may be divided into a hypnagogue stage, a lethargic stage, a rapid eye movement (REM) sleep stage, and a non-REM (NREM) sleep stage. The NREM sleep stage may be divided into stages 1-4.

In an embodiment of the present disclosure, a sleep analysis device may acquire and store sleep state related information or sleep information based on bio information. The analysis device may be provided within an electronic device or a temperature adjustment device. Further, the analysis device may be provided in an external server (e.g., cloud server).

In an embodiment of the present disclosure, the sleep score represents a user's good sleep level with a numerical value, and as the sleep score increases, a user's good sleep level may increase. The sleep score is calculated by analyzing a user's bio information and represents extracted sleep information (sleep cycle number, sleep stage distribution) with a numerical value. The sleep score may be acquired in a day unit. However, the sleep score is not limited thereto and may be measured in a time unit input by a user. Alternatively, whenever sleeping, the sleep score may be non-periodically acquired.

In an embodiment of the present disclosure, a sleep optimal temperature is a temperature that enables a user to get good sleep when the user sleeps and may be determined based on a sleep score. Further, a sleep optimal temperature may be determined based on sleep evaluation (similarity with a normal sleep pattern) as well as a sleep score.

In an embodiment of the present disclosure, a test temperature is a temperature that controls a temperature adjustment device in order to obtain data using for determining a user's sleep optimal temperature. When controlling a temperature adjustment device at a test temperature, the user's bio information may be collected and a sleep score may be determined based on the collected bio information. Further, a sleep optimal temperature may be determined based on the sleep score. In order to determine a sleep optimal temperature, bio information acquired from at least two test temperatures may be used.

In an embodiment of the present disclosure, temperature sensitivity is determined based on a change amount of a sleep score to a temperature change amount. The temperature sensitivity may be user specific information. Temperature sensitivity may be used for setting a threshold range to a sleep optimal temperature and setting a threshold range on a sleep stage basis. When temperature sensitivity is high, a user is sensitive to a temperature change and thus a threshold range of a temperature change may be narrowly set based on a sleep optimal temperature, and when temperature sensitivity is low, a user is insensitive to a temperature change and thus a threshold range of a temperature change may be widely set based on a sleep optimal temperature.

In conditions for comfortable sleep, a body temperature and a temperature (i.e., indoor temperature) are considered as major factors. When an awakening state is converted to a sleep state, a body temperature of a human generally declines, and when a sleep state is converted to an awakening state, a body temperature of a human generally rises. Therefore, by declining a peripheral temperature upon hypnagogue and by raising again a peripheral temperature upon wake-up, good sleep may be obtained.

A sleep state is divided into an REM sleep state and an NREM sleep state. Further, NREM sleep may be divided into stages 1-4 (NREM 1, NREM 2, NREM 3, and NREM 4). As a stage of NREM sleep increases (stage 1→stage 4), the sleep may be referred to as deep sleep and the entirety of NREM sleep stages 3-4 may be referred to as slow wave sleep (SWS).

In an REM sleep state, protein synthesis of a central nervous system increases, a function of a brain tissue is recovered, an oxygen consumption amount of a brain and a brain blood flow amount increase and thus the brain is functionally activated. The REM sleep state appears at 80-100 minutes after sleep, and in the REM sleep state, a fast movement of eye and irregular respiration and heartbeat number are observed together with an alpha wave of 8-13 Hz.

In an NREM sleep state, a growth hormone and a body tissue are recovered, a parasympathetic nerve is activated, less energy is used, and a body temperature is decreased and maintained. Further, a heart rate, a cardiac output, and a blood pressure are lowered. A stage of NREM sleep may be divided into four stages, as described above. In a stage 1, a theta wave of 4-7 Hzdml and a slow eye movement occur. In a stage 2, a sleep spindle wave of 12-14 Hz appears and the stage 2 is a largest portion during sleep. Stages 3-4 are referred to as SWS and represent a deep sleep state. When a delta wave of 0.5-3 Hz increases and when a delta wave is 20-50%, the sleep is classified into a stage 3, and when a delta wave is 50% or more, the sleep is classified into a stage 4.

In this way, because a sleep state has different sleep characteristics on a stage basis, when using a sleep sensor, a sleep stage may be detected. In an embodiment of the present disclosure, a temperature adjustment device for sleep uses a detected sleep state. Thereby, a sleep quality can be improved through a good sleep control based on a sleep state on a user basis, energy can be efficiently managed, and power efficiency can be improved.

In more detail, in an embodiment of the present disclosure, an actual user's sleep analysis data are collected using a sensor (e.g., sleep sensor), and the collected sleep analysis data are used. Sleep analysis data may include information about a sleep arriving time, a total sleep time, a sleep configuration, a sleep stage immediately before awakening, a wake-up delay time, a body temperature, a heartbeat number, and a discharge wavelength. The sleep arriving time is a time period from a time point at which a user has a sleep intention to a time point that arrives at sleep. The sleep time may include information about a time period between a time point at which an awakening state is converted to a sleep state and a time point period at which a sleep state is converted to an awakening state and a time at which REM sleep or NREM sleep is performed. The sleep configuration may include information about the number and time of REM sleep, the number and a time of each stage of NREM sleep, and the conversion number of REM sleep and NREM sleep. The sleep stage immediately before awakening may include information about whether a user's sleep state immediately before awakening is a REM sleep state or an NREM sleep state and a detailed stage of an NREM sleep state. The wake-up delay time is information about a time period until a time point at which a sleep intention is released after a wake-up awakening state. The sleep intention may be measured by a sleep sensor, and a method thereof will be provided in the following description.

In an embodiment of the present disclosure, a sleep score may be acquired (calculated, derived) from an extracted factor. The sleep score may be acquired in a day unit. However, the sleep score is not limited thereto and may be acquired on a preset cycle basis. Alternatively, whenever sleeping, the sleep score may be non-periodically acquired. In an embodiment of the present disclosure, a good sleep score or a good sleep index may be used with the same meaning as that of a sleep score.

A process of acquiring a sleep score or a process of acquiring and/or analyzing sleep analysis data may be referred to as a study process. Information about a peripheral environment in which a personal sleep score is highest may be acquired through such a study process. Information about a peripheral environment includes temperature information. Information about a temperature in which a sleep score is highest may be a personal good sleep temperature or a personal optimal temperature. According to the related art, because a user's actual sleep analysis data are not used, a sleep optimal temperature of each user cannot be used. However, in an embodiment of the present disclosure, sleep optimal temperature information may be acquired through a study process. When using a sleep optimal temperature, temperature adjustment that reflects a personal actual sleep characteristic can be performed and thus a comfortable sleep environment can be provided.

Further, in an embodiment of the present disclosure, sensitivity information (including temperature sensitivity) based on sleep analysis data may be acquired. Temperature sensitivity information (including individual temperature sensitivity information) represents information in which a user reacts to a temperature change. When sensitivity is high, a temperature change has a large influence on sleep, and when sensitivity is low, a temperature change has a small influence on sleep. Each person has different sensitivity. In a person having high sensitivity to a temperature, because a small temperature change has a large influence on sleep, in spite of large power consumption, it is efficient to manage a peripheral temperature in an appropriate temperature range, but in a person having low sensitivity, because a large temperature change has a small influence on sleep, by stopping operation of a temperature adjustment device or by adjusting an operation performance, it is efficient to reduce power consumption. Further, in a study process, individual temperature sensitivity information may be acquired. When using individual temperature sensitivity information, power efficiency can be enhanced and a study process of obtaining a personal good sleep temperature can be shortened. Further, when more than one user is using the temperature adjustment device, optimal efficiency of a plurality of users can be obtained based on information of a person having high sensitivity.

In the following embodiment of the present disclosure, a control of a temperature adjustment device using an electronic device will be mainly described. However, it is to be understood that this is one embodiment and does not limit operation of the temperature adjustment device to an operation control of the temperature adjustment device but may apply to a control of various peripheral devices for a good sleep control. The peripheral device may include at least one of an audio/video (AV) device, a lighting device, an oxygen generation device, a temperature adjustment device, a humidity adjustment device, a scent generation device, an audio output device, and a bed (slope change device, vibration generation device). The electronic device may control at least one of the peripheral devices to assist a user's good sleep. The electronic device may control at least one of the peripheral devices to adjust a temperature, a humidity, lighting, oxygen, an audio, a scent, and a slope and vibration of a bed. For example, sleep optimal vibration intensity may be determined using a method of determining a sleep optimal temperature. That is, a control instruction may be transmitted to determine test vibration intensity, to calculate a sleep score according to test vibration intensity to determine sleep optimal vibration intensity, and to operate the peripheral device with the determined optimal vibration intensity. With a similar method, a control instruction may be transmitted to set test information (test lighting intensity, test oxygen amount, test humidity amount, test scent concentration, and test sound volume intensity), to calculate optimal information (optimal lighting intensity, optimal oxygen amount, optimal humidity amount, optimal scent concentration, and optimal sound volume intensity) determined based on the preset test information, and to control a peripheral device based on the calculated optimal information.

Figure 2A:
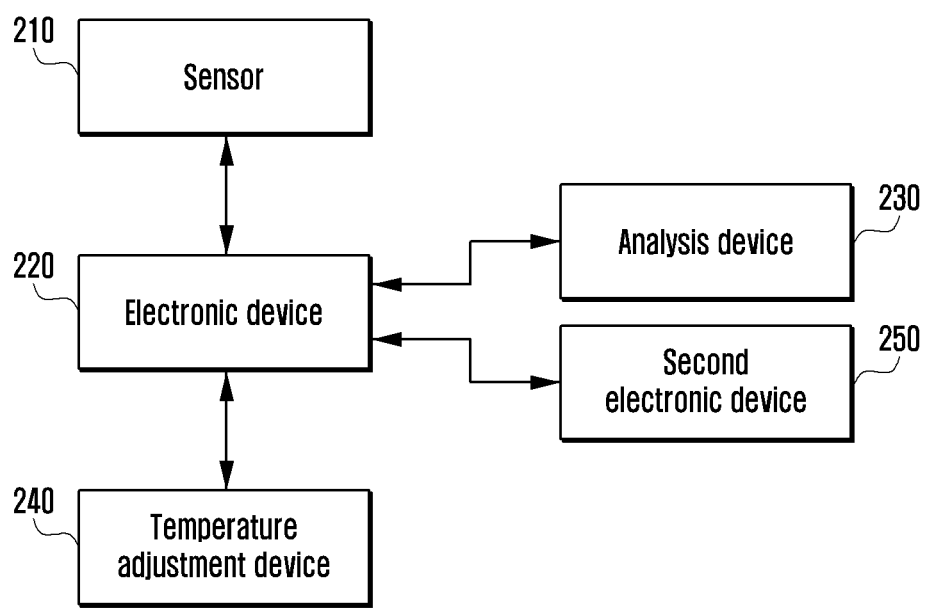
FIG. 2A is a block diagram illustrating a configuration of a temperature adjustment system according to an embodiment of the present disclosure.

FIG. 2A is a block diagram illustrating a configuration of a temperature adjustment system according to an embodiment of the present disclosure.

Referring to FIG. 2A, the temperature adjustment system may include a sensor 210, an electronic device 220, an analysis device 230, and a temperature adjustment device 240. Further, the temperature adjustment system may include a second electronic device 250. The sensor 210, the electronic device 220, the analysis device 230, and the temperature adjustment device 240 may be connected by wire or wireless. The sensor 210, the electronic device 220, the analysis device 230, the temperature adjustment device 240, and the second electronic device 250 may be the plural.

The sensor 210 may detect a user's bio signal (bio information). The bio information may be at least one of a user's blood sugar information, body temperature information, pulse information, respiration information, heartbeat information, electrocardiogram information, brainwave information, eye movement information (movement of eyeball, blink, the number of blink, movement of eyelid, and tear), and movement information. Further, the sensor 210 may additionally detect information about a sleep stage and a sleep stage duration time.

The sensor 210 may include at least one of a sleep detection sensor, a brainwave sensor, a piezoelectric sensor, a temperature detection sensor, a movement detection sensor, a bio sensor, an optical detection sensor, a gyro sensor, and an inertia sensor. In the following description, as the sensor 210, a sleep state detection sensor is mainly described, but in an embodiment of the present disclosure, a plurality of sensors described in the foregoing description as well as a sleep sensor may be used. The sensor 210 may transmit information about a detected user to the electronic device 220. The sensor 210 may be installed at various objects. For example, the sensor 210 may be mounted in a bed pad, an eyepatch, a pillow, a wristwatch, a patch, and a microwave to detect a user's bio information. The sensor 210 may use heart rate variability (HRV), respiration, piezoelectricity, body temperature, movement, electroencephalography (EEG), acceleration, and pulse in order to detect bio information.

The electronic device 220 may control the temperature adjustment device 240 using information (including bio information) about a user received from the sensor 210. In an embodiment of the present disclosure, the electronic device 220 may be a gateway or a smart home gateway, and for convenience of description, hereinafter, a term "electronic device" is used. The electronic device 220 may generate a control instruction (control signal, control message) for controlling the temperature adjustment device 240 based on user information received from the sensor 210. Further, the electronic device 220 may control the temperature adjustment device 240 using the generated control instruction. The electronic device 220 may acquire a user's sleep state related information based on user information and control the temperature adjustment device 240 based on sleep state related information. Further, the electronic device 220 may transmit user information received from the sensor 210 to the analysis device 230. The electronic device 220 may receive a user's sleep state related information from the analysis device 230. Thereafter, the electronic device 220 may generate a control instruction for controlling the temperature adjustment device 240 based on sleep state related information received from the analysis device 230 and transmit the generated control instruction to the temperature adjustment device 240. The control instruction may be an instruction that instructs operation of the temperature adjustment device 240 to operate at a specific temperature n or a sleep optimal temperature m. The temperature adjustment device 240, having received the control instruction may operate at a specific temperature n or a sleep optimal temperature m based on a temperature measured by a sensor (may be connected to the inside of the temperature adjustment device or may be directly connected to the temperature adjustment device and may receive temperature information from an external temperature sensor) that transfers temperature information to the temperature adjustment device 240. For example, when the temperature adjustment device is an air-conditioner, if a peripheral temperature is higher than a specific temperature n, the electronic device 220 may control to operate the air-conditioner to lower a peripheral temperature (air conditioning operation), and if a peripheral temperature is lower than a specific temperature n, the electronic device 220 may control to raise a peripheral temperature to a specific temperature n or to stop an operating air-conditioning function. The electronic device 220 may receive feedback information about a control instruction transmitted to the temperature adjustment device 240. Further, the electronic device 220 may receive information about a state or operation of the temperature adjustment device from the temperature adjustment device 240 and output the received information.

The electronic device 220 may include a temperature sensor. Further, the electronic device 220 may receive temperature information about a target location from an external temperature sensor. In this case, the electronic device 220 may acquire information about a present temperature. When information about a present temperature is acquired, the electronic device 220 may directly control operation of the temperature adjustment device 240. For example, the electronic device 220 may transmit a control instruction that instructs to operate to a specific temperature without information about a present temperature to the temperature adjustment device 240, and the temperature adjustment device 240 may perform an operation for arriving at a specific temperature based on the received control signal. When temperature information acquired by a temperature sensor of the electronic device 220 or the electronic device 220 exists, the electronic device 220 may control a direct operation for a specific temperature. The electronic device 220 may directly adjust on/off, intensity, and time. That is, when operating to a specific temperature n, the electronic device 220 may directly measure a peripheral temperature based on a temperature sensor and transmit an on/off instruction for operating to the specific temperature n to the temperature adjustment device 240. For example, when the temperature adjustment device 240 is an air-conditioner and when operating to a specific temperature n, if temperature information acquired by a temperature sensor of the electronic device 220 or the electronic device 220 is higher than the specific temperature n, the electronic device 220 may transmit a temperature control instruction that turns on the temperature adjustment device 240 to the temperature adjustment device 240. When operating to the specific temperature n, if temperature information acquired by the temperature sensor of the electronic device 220 or the electronic device 220 is lower than the specific temperature n, the electronic device 220 may transmit a temperature control instruction that turns off the temperature adjustment device 240 to the temperature adjustment device 240.

When a temperature sensor for measuring a peripheral temperature is located at a specific location for temperature adjustment or the electronic device, the electronic device 220 may more accurately control a temperature of a specific location. For example, when a temperature is measured based on a temperature sensor of the temperature adjustment device 240, a difference may occur between a temperature at the temperature sensor of the temperature adjustment device 240 and a temperature of a specific location in which the user attempts to adjust. However, at a specific location for temperature adjustment or at the sensor located at the electronic device, because temperature information of the specific location may be directly measured, a temperature of the specific location can be accurately adjusted and user satisfaction can be maximized.

The analysis device 230 may analyze user information (sleep information, sleep state related information) based on bio information received from the electronic device 220. For example, the user information may be a user's sleep state related information. The analysis device 230 may be included in the temperature adjustment device 240 or the electronic device 220. Further, the analysis device 230 may be included in an external server (e.g., cloud server).

The analysis device 230 may analyze a sleep state based on at least one of bio information (blood sugar information, body temperature information, pulse information, respiration information, heartbeat information, electrocardiogram information, brainwave information, eye movement information (movement of eyeball, blink, the number of blink, movement of eyelid, and tear), and movement information). The analysis device 230 may transmit analyzed sleep state related information to the electronic device 220. Further, the analysis device 230 may store the user information and analyzed sleep state related information.

The sleep state related information may include information about a sleep state such as a stage of attempting hypnagogue, a hypnagogue stage, a sleep stage, awakening, tossing and turning, and movement and information about a good sleep index, a sleep disturbance index, a hypnagogue index, a sleep index, a wake-up index, a sleep arriving time, a total sleep time, an actual wake-up time after awakening, a sleep attempt start time, a sleep start time, an awakening start time, a wake-up time, a sleep configuration score, and a sleep stage immediately before awakening.

The analysis device 230 may acquire sleep information using a study function. The sleep information may include at least one of information about a sleep score, a sleep optimal temperature, and a temperature sensitivity (individual temperature sensitivity). The analysis device 230 may obtain a sleep score, a sleep optimal temperature, and a temperature sensitivity based on sleep state related information (stage of attempting hypnagogue, hypnagogue stage, sleep stage, awakening, tossing and turning, movement, sleep time, and sleep cycle) derived from bio information. The electronic device 220 may receive sleep state related information such as a stage of attempting hypnagogue, a hypnagogue stage, a sleep stage, awakening, tossing and turning, movement, a sleep time, and a sleep cycle derived from bio information from the analysis device 230 and obtain a sleep score, a sleep optimal temperature, and a temperature sensitivity.

When a sleep score, a sleep optimal temperature, and a temperature sensitivity are calculated, the analysis device 230 may transmit sleep state related information including at least one of the sleep score, sleep optimal temperature, and temperature sensitivity to the electronic device 220.

The analysis device 230 may be formed with a sleep analysis module, a sleep evaluation module, a sleep information storage module, and a machine learning module. Further, the analysis device 230 may include at least one of the sleep analysis module, the sleep evaluation module, the sleep information storage module, and the machine learning module. The sleep analysis module may analyze sleep information based on bio information received from the electronic device 220. Bio information or sleep state related information may be stored at the sleep information storage module. The sleep evaluation module may acquire a sleep score (good sleep score, sleep evaluation related information) using data stored at the sleep information storage module. The sleep score may be stored at the sleep information storage module. The machine learning module executes study based on data stored at the sleep information storage module and stores study information at the sleep information storage module. Study information may include a sleep optimal temperature and temperature sensitivity information.

At least one of the sleep analysis module, sleep evaluation module, sleep information storage module, and machine learning module may be provided in the electronic device 220. In this case, the electronic device 220 may perform an operation of the foregoing sleep analysis module, sleep evaluation module, sleep information storage module, and machine learning module.

The temperature adjustment device 240 may perform an operation for adjusting a temperature based on control information received from the electronic device 220. As described above, the temperature adjustment device 240 includes an electronic device having a temperature adjustment function, such as an air-conditioner. The temperature adjustment device 240 may have a temperature sensor and a humidity sensor. The temperature sensor and the humidity sensor may be separately provided from the temperature adjustment device 240. That is, the temperature sensor and the humidity sensor may be provided in the electronic device 220 as well as the temperature adjustment device 240 and may be provided at a specific location to adjust a temperature. When a temperature sensor and a humidity sensor are located at the electronic device 220 or a specific location, temperature information of a specific location to control a temperature may be more accurately measured, and the temperature sensor and the humidity sensor may operate at an optimal temperature. The temperature sensor and the humidity sensor may measure a temperature and humidity of space in which the temperature adjustment device 240 operates.

The second electronic device 250 measures user information (including bio information) and transmits the user information to the electronic device 220. In an embodiment of the present disclosure, the second electronic device 250 as well as the sensor 210 may measure bio information and transmit the bio information to the electronic device 220. For example, the second electronic device 250 may be a wearable device that can communicate with the electronic device 220. The wearable device may include electronic glasses, electronic clothing, an electronic bracelet, an electronic necklace, an electronic tattoo, and a smart watch. The second electronic device 250 may acquire user information. For example, the second electronic device 250 may acquire information about a user's body temperature, an amount of exercise, a heartbeat number, a blood pressure, a respiration, a movement, eyeball information, and a moving distance.

The electronic device 220 may generate a control signal for controlling the temperature adjustment device using bio information received from the sensor 210, sleep state related information and/or sleep information received from the analysis device, and bio information received from the second electronic device 250.

The temperature adjustment system of FIG. 2A is provided for convenience of description, and in an embodiment of the present disclosure, a configuration of an entity used for adjusting a temperature is not limited to a configuration of FIG. 2A. For example, the sensor 210, the electronic device 220, the analysis device 230, and the temperature adjustment device 240 may be included in one electronic device. Further, at least two devices of the sensor 210, the electronic device 220, the analysis device 230, and the temperature adjustment device 240 may be physically included within one electronic device. For example, the sensor 210 and the electronic device 220 may constitute one electronic device, the electronic device 220 and the analysis device 230 may constitute one electronic device, and the temperature adjustment device 240 and the analysis device 230 may constitute one electronic device.

Figure 2B:
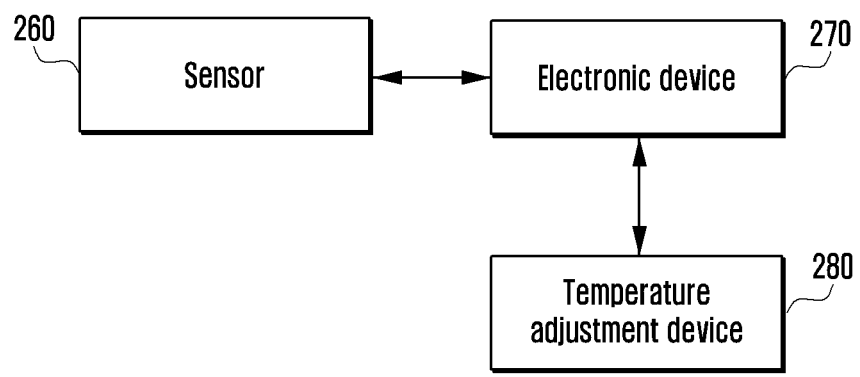
FIGS. 2B and 2C are block diagrams illustrating a configuration of a temperature adjustment system according to various embodiments of the present disclosure.

FIG. 2B is a block diagram illustrating a configuration of a temperature adjustment system according to an embodiment of the present disclosure.

Referring to FIG. 2B, the temperature adjustment system may include a sensor 260, an electronic device 270, and a temperature adjustment device 280. The sensor 260, the electronic device 270, and the temperature adjustment device 280 may be connected by wire or wireless. The temperature adjustment system may include a plurality of sensors 260 and temperature adjustment devices 280.

The sensor 260 may perform an operation and a function of the sensor 210 of FIG. 2A.

The electronic device 270 may perform an operation and a function of the electronic device 220 of FIG. 2A. Further, the electronic device 270 includes a function of the analysis device 230 of FIG. 2A.

The temperature adjustment device 280 may perform an operation and a function of the temperature adjustment device 240 of FIG. 2A.

A description of an operation and a function of each entity of FIG. 2B corresponding to each entity of FIG. 2A corresponds to that of FIG. 2A and therefore a detailed description thereof will be omitted.

The electronic device 270 may set a plurality of temperatures to a test temperature, control the temperature adjustment device to each test temperature, acquire bio information corresponding to each test temperature, calculate a sleep score corresponding to each test temperature based on the acquired bio information, determine a sleep optimal temperature based on the calculated sleep score, and transmit a control instruction for controlling the temperature adjustment device to the temperature adjustment device based on the sleep optimal temperature.

The electronic device 270 may acquire sleep stage information based on the bio information and generate the temperature control instruction based on the sleep stage information and the sleep optimal temperature. Further, the electronic device 270 may transfer the bio information to the sleep analysis device, receive sleep information from the sleep analysis device, and determine the sleep optimal temperature based on the sleep information.

The electronic device 270 may acquire sleep state related information based on the bio information and acquire the sleep score based on the sleep state related information. The electronic device 270 may acquire a first sleep score based on acquired bio information when applying a first test temperature, acquire a second sleep score based on acquired bio information when applying second test temperature, and determine the sleep optimal temperature based on the first sleep score and the second sleep score. The sleep evaluation score may be determined based on a good sleep index and a sleep disturbance index, and the good sleep index may be determined based on at least one of a hypnagogue index, a sleep index, and a wake-up index.

Further, the electronic device 270 may determine temperature sensitivity based on bio information. Temperature sensitivity may be determined based on a first sleep score of a first test temperature, a second sleep score of a second test temperature, and a temperature difference between the first test temperature and the second test temperature. The electronic device 270 may adjust a threshold range to correspond to temperature sensitivity. That is, the electronic device 270 may generate a temperature control instruction based on a threshold range corresponding to a sleep optimal temperature and the temperature sensitivity. Further, the electronic device 270 may acquire sleep stage information and may differently apply a threshold range corresponding to temperature sensitivity on a sleep stage basis based on sleep stage information.

Further, the electronic device 270 may generate a control instruction that raises a peripheral temperature when detecting a final REM sleep state in entire sleep.

The electronic device 270 may acquire a sleep score of the sleep optimal temperature, compare the sleep score with a preset threshold value, and perform at least one of a study operation or a feedback interface output operation, if the sleep score is smaller than a preset threshold value.

Figure 2C:
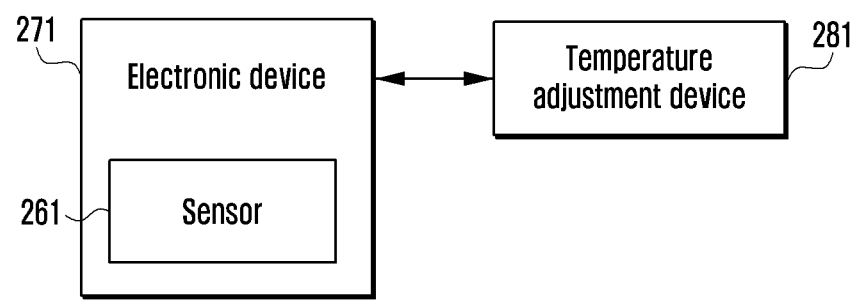

FIG. 2C is a block diagram illustrating a configuration of a temperature adjustment system according to an embodiment of the present disclosure.

Referring to FIG. 2C, the temperature adjustment system may include an electronic device 271 and a temperature adjustment device 281. The electronic device 271 may include a sensor 261. That is, in FIG. 2B, the sensor 260 provided at the outside of the electronic device 270 communicates with the electronic device 270 to transfer a sensing result, and in FIG. 2C, the electronic device 271 may directly measure bio information or may measure a peripheral temperature through the sensor 261 provided within the electronic device 271.

The sensor 261 may perform an operation and a function of the sensor 210 of FIG. 2A.

The electronic device 271 may perform an operation and a function of the electronic device 220 of FIG. 2A. Further, the electronic device 271 may perform a function of the analysis device 230 of FIG. 2A and an operation and a function of the sensor 210 of FIG. 2A.

The temperature adjustment device 281 may perform an operation and a function of the temperature adjustment device 240 of FIG. 2A.

Further, the electronic device 271 may perform an operation and a function of the electronic device 270 of FIG. 2B. In this case, in FIG. 2B, the electronic device 270 may receive bio information from the sensor 260, and the electronic device 271 of FIG. 2C may directly acquire peripheral temperature information through the sensor 261 provided therein.

Figure 2D:
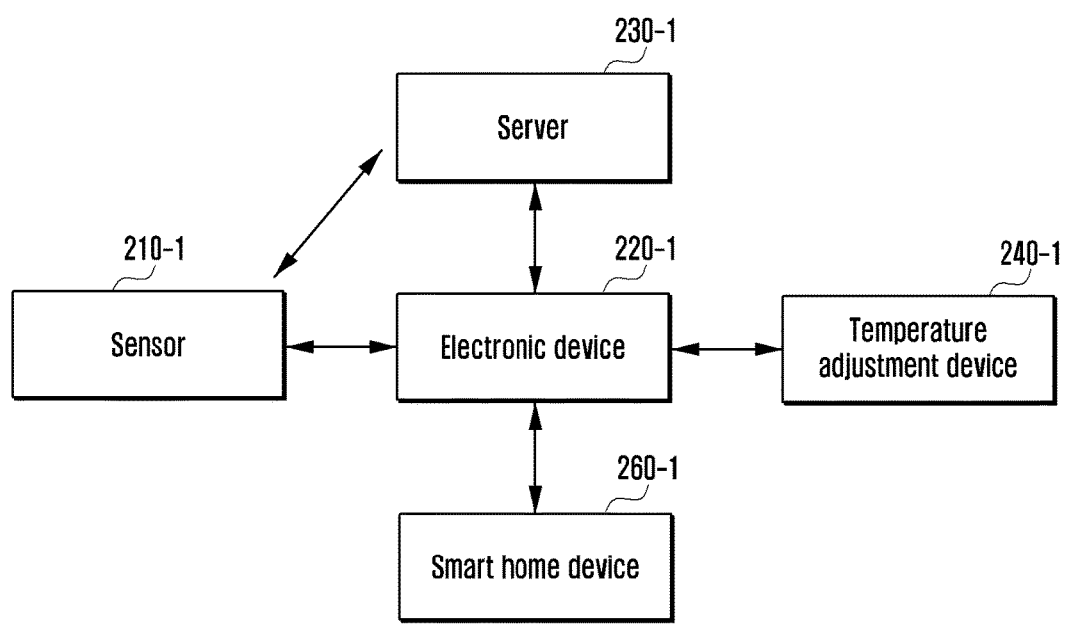
FIG. 2D is a block diagram illustrating a configuration of a smart home system according to an embodiment of the present disclosure.

FIG. 2D is a block diagram illustrating a configuration of a smart home system according to an embodiment of the present disclosure.

Referring to FIG. 2D, the smart home system may include a sensor 210-1, an electronic device 220-1, a server 230-1, a temperature adjustment device 240-1, and a smart home device 260-1. In FIG. 2D, entities corresponding to each entity of FIG. 2A may perform a function of each entity of FIG. 2A.

The sensor 210-1, the electronic device 220-1, the temperature adjustment device 240-1, and the smart home device 260-1 each may be the plural.

The sensor 210-1 may detect a user's bio signal (bio information). The bio information may be at least one of a user's blood sugar information, body temperature information, pulse information, respiration information, heartbeat information, electrocardiogram information, brainwave information, eye movement information (movement of eyeball, blink, the number of blink, movement of eyelid, and tear), and movement information. Further, the sensor 210-1 may additionally detect information about a sleep stage and a sleep stage duration time. The sensor 210-1 corresponds to the sensor 210 of FIG. 2A and therefore a detailed description thereof will be omitted.

The electronic device 220-1 may be a gateway or a terminal for controlling home appliances. The gateway may be a smart home gateway. The smart home gateway includes the temperature adjustment device 240-1 and may be a gateway for controlling the smart home device 260-1.

The electronic device 220-1 may control the temperature adjustment device 240-1 and the smart home device 260-1 based on bio information received from the sensor 210-1. For example, the electronic device 220-1 may receive sleep information or sleep state related information from the server 230-1. The electronic device 220-1 may generate a control instruction for controlling the temperature adjustment device 240-1 or the smart home device 260-1 according to a sleep state and a sleep stage based on information received from the server 230-1 and transmit the control instruction to a corresponding device. The electronic device 220-1 corresponds to the electronic device 220 of FIG. 2A and therefore a detailed description thereof will be omitted.

The server 230-1 may be a cloud server. The server 230-1 may analyze sleep information and sleep state related information based on bio information received from the electronic device 220-1. The server 230-1 may directly receive bio information from the sensor 210-1 and transmit sleep information and/or sleep state related information to the electronic device 220-1. The sleep state related information may include at least one of information about a sleep state such as a stage of attempting hypnagogue, a hypnagogue stage, a sleep stage, an awakening, tossing and turning, and movement and information about a good sleep index, a sleep disturbance index, a hypnagogue index, a sleep index, a wake-up index, a sleep arriving time, a total sleep time, an actual wake-up time after awakening, a sleep attempt start time, a sleep start time, an awakening start time, a wake-up time, a sleep configuration score, and a sleep stage immediately before awakening. The sleep information may include at least one of information about a sleep score, a sleep optimal temperature, and a temperature sensitivity (individual temperature sensitivity). The server 230-1 may correspond to the analysis device 230 of FIG. 2A.

The temperature adjustment device 240-1 adjusts a temperature based on control information received from the electronic device 220-1 and may include an air-conditioner. The temperature adjustment device 240-1 corresponds to the temperature adjustment device 240 of FIG. 2A.

The smart home device 260-1 may connect, monitor, and control a home appliance (television, air-conditioner, and refrigerator), an energy consumption device (water supply, electricity, and air conditioning and heating), a security device (door lock, surveillance camera) to an electronic device (terminal or gateway) with a communication network. For example, the temperature adjustment device 240-1 may be an example of a smart home device. Therefore, an operation of the smart home device 260-1 may correspond to an operation of a temperature adjustment device in an embodiment of the present disclosure.

Figure 2E:
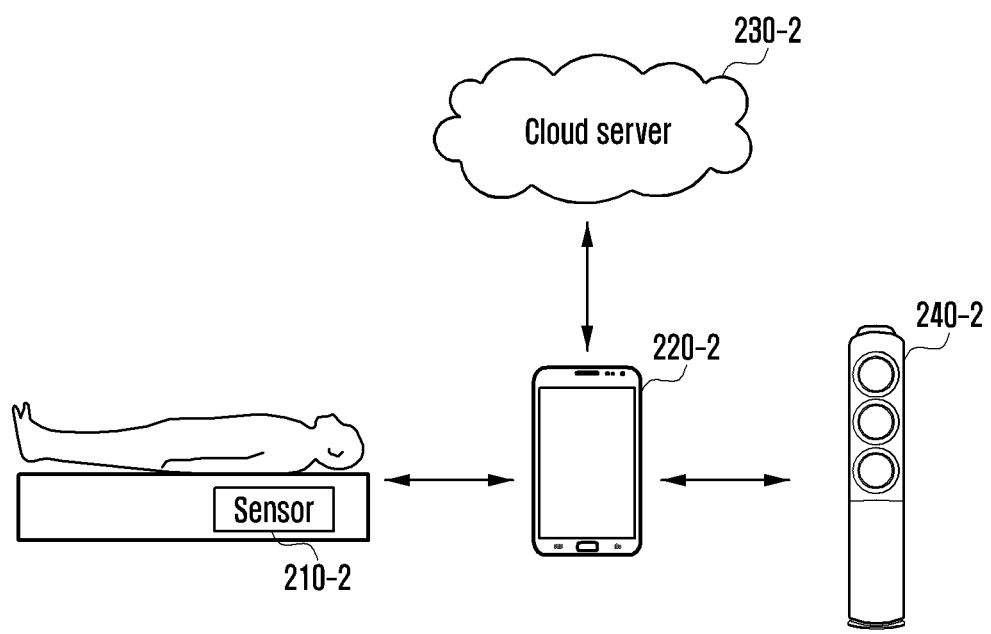
FIG. 2E is a diagram illustrating a smart home system according to an embodiment of the present disclosure.

FIG. 2E is a diagram illustrating a smart home system according to an embodiment of the present disclosure.

Referring to FIG. 2E, the smart home system may include a sensor 210-2, an electronic device 220-2, a cloud server 230-2, and a temperature adjustment device 240-2. In FIG. 2E, entities corresponding to each entity of FIG. 2D may perform a function of each entity of FIG. 2D.

Figure 3A:
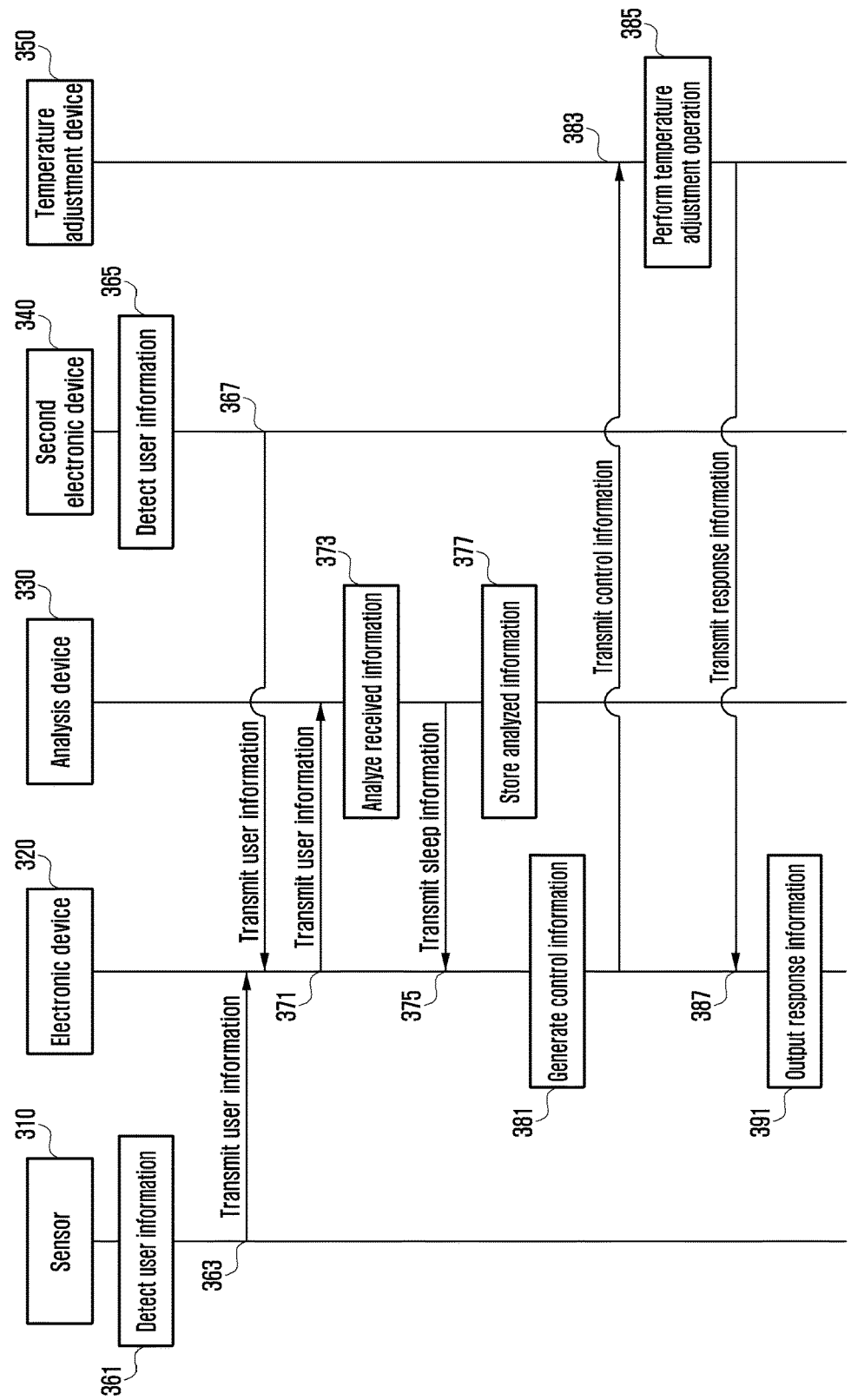
FIG. 3A is a message flow diagram illustrating operation of a temperature adjustment system according to an embodiment of the present disclosure.

FIG. 3A is a message flow diagram illustrating operation of a temperature adjustment system according to an embodiment of the present disclosure.

Referring to FIG. 3A, a sensor 310 may detect user information at operation 361. The user information may be information (bio information) about a bio signal. The sensor 310 may transmit the detected bio information to an electronic device 320 at operation 363. The sensor 310 and the electronic device 320 may be connected through a wire or wireless interface. The operations of detecting user information and transmitting detected user information in the sensor 310 may periodically or non-periodically occur. And, while performing an operation of FIG. 3A, multiple occurrences of detection and an operation of transmitting detected information may be performed.

A second electronic device 340 may detect user information (bio information) at operation 365. The second electronic device 340 may transmit the detected information to the electronic device 320 at operation 367. The second electronic device 340 and the electronic device 320 may be connected through a wire or wireless interface. The operations of detecting user information and transmitting detected user information in the second electronic device 340 may periodically or non-periodically occur. And, while performing an operation of FIG. 3A, multiple occurrences of detection and an operation of transmitting detected information may be performed.

The electronic device 320 may transmit user information (bio information) received from the sensor 310 and/or the second electronic device 340 to an analysis device 330 at operation 371.

The analysis device 330 may analyze user information (bio information) received from the electronic device 320 at operation 373. At the analysis device 330, a database (DB) for analyzing user information may be stored. The analysis device 330 may analyze user information (bio information) received from the electronic device 320 and generate sleep state related information and/or sleep information. The sleep state related information may include information about a sleep state such as a stage of attempting hypnagogue, a hypnagogue stage, a sleep stage, an awakening, a tossing and turning, and a movement and information about a good sleep index, a sleep disturbance index, a hypnagogue index, a sleep index, a wake-up index, a sleep arriving time, a total sleep time, an actual wake-up time after awakening, a sleep attempt start time, a sleep start time, an awakening start time, a wake-up time, a sleep configuration score, and a sleep stage immediately before awakening. The sleep information may include at least one of information about a sleep score, a sleep optimal temperature, and a temperature sensitivity. The analysis device 330 may transmit sleep state related information and/or sleep information to the electronic device 320 at operation 375. The analysis device 330 may store user information and/or sleep information at operation 377.

The analysis device 330 may transmit the analyzed sleep state related information to the electronic device 320. Further, the analysis device 330 may store the user information and the analyzed sleep state related information. The analysis device 330 may acquire information about a sleep score, sleep optimal temperature, and sensitivity using a study function. The analysis device 330 may transmit information about a sleep score, sleep optimal temperature, and sensitivity to the electronic device 320.

When the electronic device 320 and the analysis device 330 are formed in the same electronic device, the operations 371 to 381 may be performed as an internal operation of an electronic device including the electronic device 320 and the analysis device 330.

The electronic device 320 may generate a control instruction for controlling a temperature adjustment device 350 based on sleep state related information and/or sleep information received from the analysis device 330 at operation 381. The control instruction for controlling the temperature adjustment device 350 may include a control instruction such as a sleep optimal temperature setting, a hypnagogue optimal temperature setting, an individual temperature sensitivity setting, a sensitivity setting on a step basis, and a feedback information setting. Further, the control instruction is not limited thereto, and in an embodiment of the present disclosure, the control instruction may include a control instruction for controlling a temperature adjustment device.

The electronic device 320 may transmit the generated control information to the temperature adjustment device 350 at operation 383.

The temperature adjustment device 350 may perform a temperature adjustment operation based on control information received from the electronic device 320 at operation 385. The temperature adjustment device 350 may transmit response information to the electronic device 320 at operation 387. The response information may be feedback information. The response information may be information notifying of an operation of the temperature adjustment device 350 for a control instruction received from the electronic device 320. Further, the response information may include state information (e.g., load state, system efficiency state) of the temperature adjustment device 350.

The electronic device 320 may output the received response information (may be referred to as feedback information) at operation 391. For example, the electronic device 320 may output operation state information, temperature information, load state information, and system efficiency information of the temperature adjustment device 350, and information about whether to perform an operation corresponding to the control information. For example, a display unit (display in the display of the electronic device) and a sound source output unit (feedback output based on voice) of the electronic device 320 may output the response information. Further, the feedback information may be information that requests evaluation of the temperature control adjustment device to the user. For example, as response information, information such as "Please evaluate a good sleep score", "Were you cold during sleep?", "A temperature was appropriate during sleep?" may be output. A user using an electronic device may input sleep evaluation information to correspond to the feedback information. For example, the user may input sleep satisfaction (score, character, symbol, and voice).

Figure 3B:
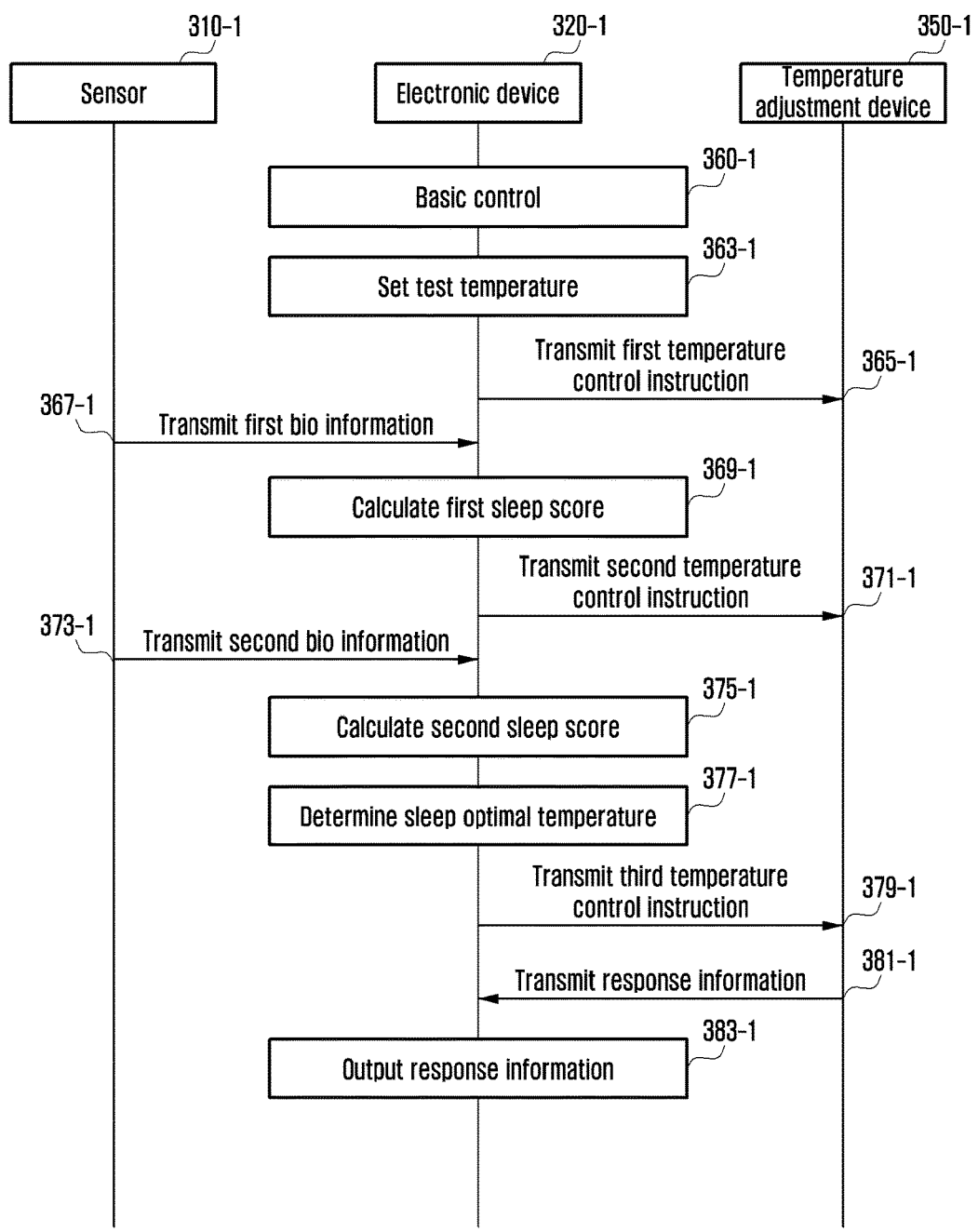
FIG. 3B is a message flow diagram illustrating operation of a temperature adjustment system according to an embodiment of the present disclosure.

FIG. 3B is a message flow diagram illustrating operation of a temperature adjustment system according to an embodiment of the present disclosure. A general operation of a sensor, electronic device, and temperature adjustment device corresponds to an operation of FIG. 3A and therefore a detailed description thereof will be omitted.

Referring to FIG. 3B, a sensor 310-1 may detect bio information and provide the bio information to an electronic device 320-1. The electronic device 320-1 may operate a temperature adjustment device 350-1 based on a test temperature, and when the temperature adjustment device 350-1 operates at a test temperature, the electronic device 320-1 may receive bio information from the sensor 310-1. The electronic device 320-1 may calculate a sleep score based on bio information and determine a sleep optimal temperature based on the sleep score. The electronic device 320-1 may transmit a control instruction for controlling the temperature adjustment device 350-1 based on the determined sleep optimal temperature.

Hereinafter, each operation will be described.

The electronic device 320-1 may operate in a basic control state at operation 360-1. The basic control state corresponds to a basic control segment operation of FIG. 4 and therefore a detailed description thereof will be omitted. The electronic device 320-1 may set a test temperature at operation 363-1. A plurality of test temperatures (first test temperature, second test temperature) may be set. A sleep score of a first test temperature may be calculated and a second test temperature may be set instead of setting a plurality of test temperatures at one time.

The electronic device 320-1 transmits a first temperature control instruction to the temperature adjustment device 350-1 at operation 365-1. The temperature adjustment device 350-1 operates at a first test temperature based on a temperature control instruction. When the temperature adjustment device 350-1 operates at a first test temperature, the sensor 310-1 may collect a user's bio information. The sensor 310-1 may transmit bio information collected to correspond to the first test temperature to the electronic device 320-1 at operation 367-1. The electronic device 320-1 may calculate a first sleep score based on first bio information at operation 369-1. The first sleep score is a sleep score corresponding to the first test temperature.

Similarly, the electronic device 320-1 transmits a second temperature control instruction to the temperature adjustment device 350-1 at operation 371-1. The temperature adjustment device 350-1 operates at a second test temperature based on the temperature control instruction. When the temperature adjustment device 350-1 operates at a second test temperature, the sensor 310-1 may collect a user's bio information. The sensor 310-1 may transmit the bio information collected to correspond to the second test temperature to the electronic device 320-1 at operation 373-1. The electronic device 320-1 may calculate a second sleep score based on second bio information at operation 375-1. The second sleep score is a sleep score corresponding to the second test temperature.

The electronic device 320-1 may determine a sleep optimal temperature at operation 377-1. The electronic device 320-1 may determine a sleep optimal temperature based on the first sleep score and the second sleep score. The electronic device 320-1 may determine a temperature having a higher sleep score as a sleep optimal temperature. The electronic device 320-1 may transmit a third temperature control instruction for operating to the determined sleep optimal temperature to the temperature adjustment device 350-1 at operation 379-1. The temperature adjustment device 350-1 may operate at a sleep optimal temperature based on the third temperature control instruction. The temperature adjustment device 350-1 may transmit response information to the electronic device 320-1 at operation 381-1. The electronic device 320-1 may output response information at operation 383-1.

Figure 4:
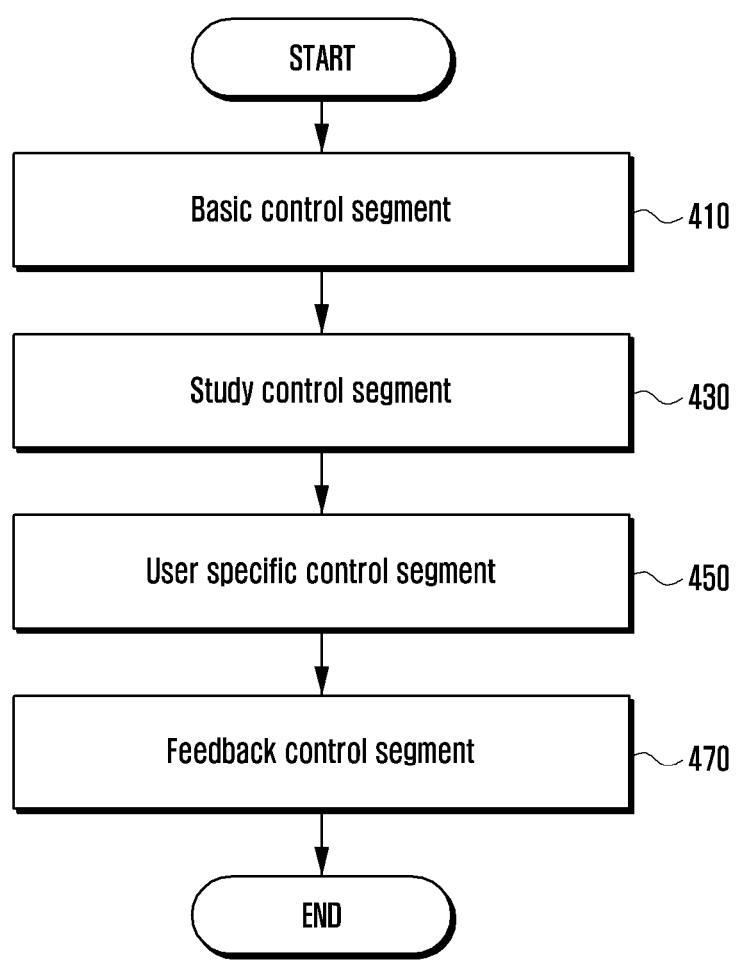
FIG. 4 is a flowchart illustrating an operation segment according to an embodiment of the present disclosure.

FIG. 4 is a flowchart illustrating an operation segment according to an embodiment of the present disclosure.

Referring to FIG. 4, in an embodiment of the present disclosure, an operation segment may be divided into a basic control segment 410, a study control segment 430, a user specific control segment 450, and a feedback control segment 470. At least one segment of each segment may be omitted, and an embodiment of the present disclosure does not always operate at the four segments.

Operation 410 is a basic control segment, and the basic control segment is a segment that operates a temperature adjustment device using user information received from the sensor with a preset operation method instead of a user's sleep score and sensitivity score.

Operation 430 is a study control segment, and the study control segment is a segment that acquires a user's sleep score and/or sensitivity score using user information received from the sensor and is a segment that operates a temperature adjustment device while adjusting a test temperature in order to determine an optimal temperature on a user basis. User information received from the sensor may be used.

Operation 450 is a user specific control segment, and the user specific control segment is a segment that operates the temperature adjustment device using an optimal temperature and/or sensitivity on a user basis acquired at the study control segment. Further, user information received from the sensor may be together used.

Operation 470 is a feedback control segment. Even when operation 450 is performed, a sleep score may be continuously calculated. If a sleep score is equal to or less than a preset first threshold value, the temperature adjustment device is controlled to return again to the study control segment 430. If a sleep score is equal to or less than a preset second threshold value, the temperature adjustment device outputs notification to the user and operates based on the user's additional input information.

Hereinafter, each operation of FIG. 4 will be described.

Operation 410 is a basic control segment. The basic control segment is an operation before study. The basic control segment is a segment in which user information does not exist before study or is a segment in which user information is insufficient when operating with a study control segment or a user specific control segment and is a segment that operates based on general setting or default setting. A default setting may be previously set to correspond to user information such as age, sex, height, weight, and sleep style (information about whether a user prefers a high temperature or a low temperature during sleep). For example, the default setting may be a default setting when the age is in the twenties, a default setting when the age is in the thirties, a default setting when sex is a man, and a default setting when sex is a woman. A default setting may be determined in consideration of a plurality of elements in the elements.

Upon awakening, a sleep optimal temperature $Ts=Ta-Ks$ is obtained using K, which is a difference between an optimal temperature Ta and a sleep optimal temperature Ts and Ks, which is a previously defined value. Because user information does not exist, an individual user's temperature sensitivity information is not considered. However, even if studied individual user's sensitivity is not considered, preset temperature sensitivity information may be used. That is, a sensitivity option divided into at least two levels in system setup may be applied, and preset temperature sensitivity information may be applied according to a user selection.

Even if an individual user's sensitivity is not considered, temperature sensitivity on a sleep stage basis may be considered.

Figure 5:
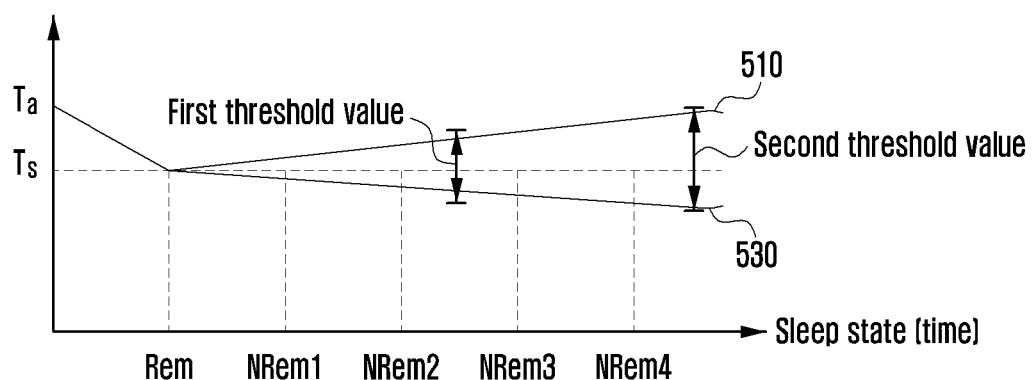
FIG. 5 is a graph illustrating a method of applying temperature sensitivity on a sleep stage basis according to an embodiment of the present disclosure.

FIG. 5 is a graph illustrating a method of applying temperature sensitivity on a sleep stage basis according to an embodiment of the present disclosure.

Temperature sensitivity on a sleep stage basis is sensitivity in consideration of a characteristic of a sleep stage. For example, in the electronic device, temperature sensitivity information on a sleep stage basis of Table 1 may be stored.

TABLE 1

| Threshold | REM | NREM | | | |
|---|---|---|---|---|---|
| Range | value 0 | NREM1 | NREM2 | NREM3 | NREM4 |
| | | ±value 1 | ±value 2 | ±value 3 | ±value 4 |

A threshold range value n corresponding to each sleep stage may be previously stored. As a sleep stage increases, values may increase. For example, values may be set in order of value 0<=value 1<=value 2<=value 3<=value 4. For example, a value 0 may be set to 0, a value 1 may be set to 0.5, a value 2 may be set to 1, a value 3 may be set to 1.5, and a value 4 may be set to 2.

In a light sleep stage (e.g., NREM sleep stages 1 and 2) on a sleep stage basis, because light sleep is sensitive to a temperature change, the light sleep has high temperature sensitivity, and in deep sleep (e.g., NREM sleep stages 3 and 4), because deep sleep is less sensitive to a temperature change, the deep sleep has relatively low temperature sensitivity. When applying temperature sensitivity on a sleep stage basis, in a light sleep stage, because temperature sensitivity is high, it is controlled to have a small temperature difference from a sleep optimal temperature. That is, in a light sleep stage, the temperature adjustment device may be controlled within a narrow threshold range from a sleep optimal temperature according to a preset threshold range, and in a deep sleep stage, the temperature adjustment device may be controlled within a wide threshold range from a sleep optimal temperature according to a preset threshold range.

Referring to FIG. 5, when the user sleeps at a comfortable temperature Ts, as advancing from REM sleep to deep stage of NREM sleep, it may be determined that a difference between a comfortable temperature and an actual temperature increases during sleep.

For example, in a light sleep stage, a first threshold value of a temperature difference is set and a peripheral temperature may be controlled to be adjusted within a first threshold value range from an optimal temperature. In a deep sleep stage, because temperature sensitivity is relatively low, a temperature difference from an optimal temperature may be controlled to be larger than that in a light sleep stage. For example, in a deep sleep stage, a second threshold value of a temperature difference may be set and a peripheral temperature may be adjusted within a second threshold value range from a sleep optimal temperature.

Temperature sensitivity on a sleep stage basis may use a previously defined value. When a preset temperature is SPr in REM sleep, sleep stages of NREM stages 1-4 are SPn1-4, a temperature on a sleep stage basis may be controlled in order of Ts<=SPr<=SPn1<=SPn2<=SPn3<=SPn4. This means that the temperature adjustment device operates, as in a temperature change curve 510. A temperature change curve 510 reflects a case in which a peripheral temperature naturally rises when the temperature adjustment device stops operation or when the temperature adjustment device operates with operation weaker than operation for maintaining a sleep optimal temperature. For example, when the temperature adjustment device does not operate, if a peripheral temperature is higher than a sleep optimal temperature, the temperature adjustment device may operate, as in the temperature change curve 510.

However, a temperature change curve 530 reflects a case in which a peripheral temperature naturally declines when the temperature adjustment device stops operation or when the temperature adjustment device operates weaker than when maintaining a sleep optimal temperature. For example, when the temperature adjustment device does not operate, if a peripheral temperature is lower than a sleep optimal temperature, the temperature adjustment device may operate, as in the temperature change curve 530. In this case, a temperature on a sleep stage basis may be controlled in order of Ts>=SPr>=SPn1>=SPn2>=SPn3>=SPn4.

When operating the temperature adjustment device in order to continuously maintain a temperature Ts without considering a characteristic on a sleep stage basis, a user's sleep comfort may be improved, but power efficiency deteriorates. When the temperature adjustment device operates by applying temperature sensitivity on a sleep stage basis, as in 510 or 530, power may be efficiently managed while minimizing an influence on sleep.

The operation uses a characteristic in which temperature sensitivity is largest in REM sleep and in which temperature sensitivity is small as advancing to a deep stage in NREM sleep in a sleep stage. In REM sleep, because a body function of adjusting a body temperature is deteriorated, large temperature sensitivity enables easy good sleep. When the user attempts to sleep in a bed, until the user sleeps, the temperature adjustment device slowly declines an indoor temperature to Ts. While the user sleeps, the temperature adjustment device operates the air-conditioner to a temperature of SPr and SPn1-4 according to a sleep stage determined in the sleep analysis module. When it is determined that a sleep stage is a final REM stage before wake-up by a previously defined value, the temperature adjustment device slowly raises a temperature and controls an indoor temperature to arrive at Ta upon wake-up.

As described above, at the basic control segment 410, the temperature adjustment device is controlled using preset information. The temperature adjustment device may perform an operation of a basic control segment according to a basic control instruction of the electronic device. Further, a basic control segment operation may be performed according to a basic control segment operation instruction directly input to the temperature adjustment device instead of through the electronic device. A control instruction of the study control segment 430 or the user specific control segment 450 is input, but even when study information, user information, or sleep information for performing the control instruction is insufficient, operation of the basic control segment 410 may be performed.

Operation 430 is a study control segment. A study control is operation that acquires a sleep optimal temperature and/or individual temperature sensitivity information based on a basic control. Further, the study control is operation that collects user information acquired through the sensor. At a study period, by changing a sleep optimal temperature, an individually optimized temperature is obtained. When obtaining an individually optimized temperature, by changing a value K, a sleep score of each sleep may be acquired, and an individually optimized temperature may be acquired based on the sleep score. Further, by changing an optimal temperature for test, a sleep score of each sleep may be acquired, and an individually optimized temperature may be acquired based on the sleep score. The test temperature means a random sleep optimal temperature for study.

TABLE 2

|  | Sleep 1 | Sleep 2 | Sleep 3 | Sleep 4 |
| --- | --- | --- | --- | --- |
| Test temperature | 22 | 23 | 23.5 | 22.5 |
| Sleep score | 7 | 8 | 7 | 8.5 |

Table 2 represents a sleep score on a test temperature basis. For example, at a test temperature of Table 2, when a sleep score of each sleep is acquired, if a test temperature is 22.5° C., the sleep score is most highly represented as 8.5 point and thus a user's sleep optimal temperature may be determined to 22.5° C. (When a result of Table 2 is derived, it is assumed that other factors that have an influence on sleep, except for a test temperature are the same on each test basis).

Figure 6:
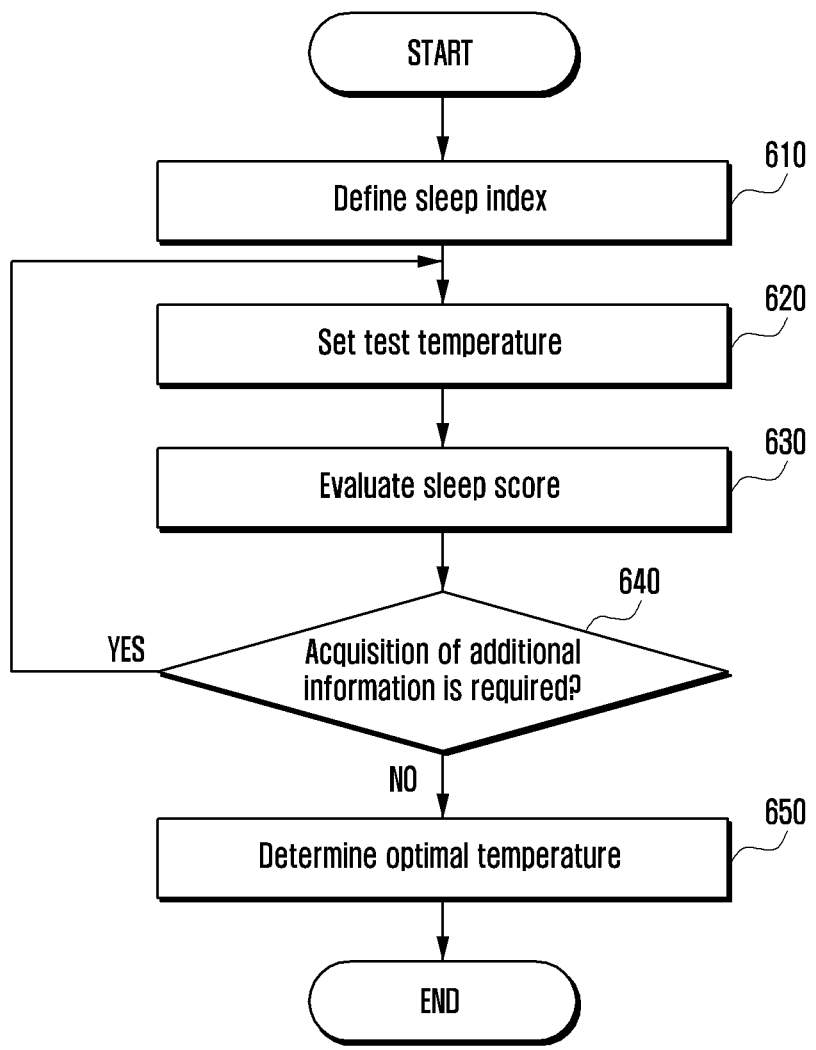
FIG. 6 is a flowchart illustrating a method of determining an individual sleep optimal temperature according to an embodiment of the present disclosure.

FIG. 6 is a flowchart illustrating a method of determining an individual sleep optimal temperature according to an embodiment of the present disclosure.

Referring to FIG. 6, the temperature adjustment system may determine a sleep related index at operation 610. The sleep related index may be previously defined. The sleep related index is used for calculating a sleep score. A method of calculating a sleep score and a factor to be considered may be changed according to a definition of the sleep related index. A method of defining a sleep related index will be described in the following description.

The temperature adjustment system determines a test temperature at operation 620. The test temperature means a random sleep optimal temperature. After a test temperature is determined, the temperature adjustment system performs a temperature adjustment operation based on the determined test temperature.

When the temperature adjustment device operates by a test temperature, a sleep score of each test temperature is acquired at operation 630. The sleep score may be determined based on a sleep related index and user information received from the sensor. The sleep score is acquired, and the acquired sleep score and related data may be stored and managed.

The temperature adjustment device may determine whether acquisition of additional information is required at operation 640. The temperature adjustment device may determine whether acquisition of additional information is required based on whether the preset execution number of sleep score has been acquired, whether a sleep score has been acquired at a preset range of test temperature, or whether a sleep score of a preset threshold value or more has been acquired. If acquisition of additional information is required due to lack of test data, the process continues at operation 620. If acquisition of additional information is not required, the process continues at operation 650.

The temperature adjustment device determines a user optimal temperature at operation 650. The user optimal temperature may be determined based on a sleep score. At sleep scores corresponding to a plurality of each test temperature, a test temperature having a highest sleep score may be determined as a user optimal temperature.

Hereinafter, each operation of FIG. 6 will be described. A sleep related index may be defined at operation 610. A sleep related index is used for deriving a sleep score.

An index of Table 3 may be used as a sleep related index.

TABLE 3

| Sleep score | Good sleep index | Sleep disturbance index | Hypnagogue index | Sleep index | Wake-up index |
|---|---|---|---|---|---|
| S | GNSI | SDI | HGI | SI | HPI |

| Sleep arriving index | Total sleep time | Actual wake-up time | Sleep attempt time | Sleep start time | Awakening start time |
|---|---|---|---|---|---|
| $T_{dhg}$ | $T_{ds}$ | $T_{dhp}$ | $T_{ts}$ | $T_s$ | $T_a$ |

TABLE 3-continued

| Wake-up time | Sleep configuration score | Sleep stage immediately before awakening |
|---|---|---|
| $T_w$ | SCS | $S_a$ |

An evaluation target time of a sleep score may be a time period from a time point at which a user lies down in a bed for sleep to a time point at which a user leaves from the bed after wake-up. Evaluation of the sleep score may be determined in consideration of a good sleep index and a sleep disturbance index. For example, a sleep evaluation score S may be determined to a sleep evaluation score S=good sleep index GNSI−sleep disturbance index SDI.

The good sleep index SNSI may be represented with a score by information collected from the sensor. The good sleep index GNSI may be determined based on at least one of the hypnagogue index HGI, the sleep index SI, and the wake-up index GPI. For example, the GNSI may be determined as GNSI=a*HGI+b*SI+(1−a−b)*GPI. The variables a and b may be weight value information.

The hypnagogue index HGI may be determined based on a sleep arriving time $T_{dhg}$. The sleep arriving time $T_{dhg}$ is a time period from a sleep attempt start time $T_{ts}$ to a sleep start time $T_s$. For example, $T_{dhg}$ may be determined as $T_{dhg}=T_s-T_{ts}$.

In this case, the sleep attempt start time $T_{ts}$ and the sleep start time $T_s$ may be determined based on user information received from the sensor. For example, information about a sleep attempt start time and a sleep start time may be acquired based on a user's movement information detected by the sensor.

The sleep index SI may be determined based on at least one of the total sleep time $T_{ds}$ and the sleep configuration score SCS. The total sleep time $T_{ds}$ is a time period from the sleep start time $T_s$ to the awakening start time $T_a$. For example, $T_{ds}$ may be determined as $T_{ds}=T_s-T_a$. A range of the total sleep time may be set. A score may be given according to a corresponding range of the total sleep time. For example, a score may be given to the total sleep time, as shown in Table 4.

TABLE 4

| Total sleep time | Score |
|---|---|
| less than 4 hours | A |
| 4-5 hours | B |
| 5-6 hours | C |
| 6-7 hours | D |
| 7-8 hours | E |
| 8 hours or more | F |

A sleep configuration score SCS may be determined based on sleep stage distribution and the sleep cycle number. In this case, a user's age or sex may be considered. That is, even in the same sleep stage distribution and the sleep cycle number, when age or sex is different, different scores may be given. For example, as shown in Table 5, a sleep configuration score may be given.

TABLE 5

| The number of sleep cycle | NREM stage 1-2 distribution | NREM stage 3-4 distribution | REM stage distribution | Score |
|---|---|---|---|---|
| 5.5 times | 55% | 20% | 25% | 90 |
| 8 times | 50% | 5% | 45% | 60 |

The sleep cycle is a cycle in which REM→NREM→REM→NREM→REM state are repeated during sleep. A cycle in which REM sleep and NREM sleep each occur one time is 1 cycle. In Table 5, when the number of the sleep cycle is 5.5 times, the number of sleep cycles is appropriate, an NREM sleep time occupies 75%, and a sleep configuration score has a high score. However, when the number of sleep cycles is 8 times, a deep NREM sleep time is short, a REM sleep time occupies 45% and thus a user does not get sound sleep and a sleep configuration score is low. A score according to the number of sleep cycles and sleep stage distribution is determined based on statistics and may be previously set to the temperature adjustment system. The number of sleep cycles and sleep stage distribution may be acquired based on user information transmitted by the sensor during sleep. For example, as described above, waves discharged at each stage of REM, NREM, and NREM are different. A sleep cycle and sleep stage distribution may be determined based on the waves.

The wake-up index HPI may be determined based on at least one of an actual wake-up time $T_{dhp}$ after awakening and a sleep stage $S_a$ immediately before awakening. The actual wake-up time after awakening may be a time period from the awakening start time $T_a$ to the wake-up time $T_w$. For example, $T_{dhp}$ may be determined as $T_{dhp}=T_w-T_a$. As the actual wake-up time $T_{dhp}$ after awakening is short, the wake-up index HPI may be highly represented.

Further, when an REM sleep stage is SaREM, NREM stage 1 is Sa1, NREM stage 2 is Sa2, NREM stage 3 is Sa3, and NREM stage 4 is Sa4, the wake-up index HPI may be applied in order of SaREM>Sa1>Sa2>Sa3>Sa4.

The following is a description of sleep inertia. Sleep inertia indicates a state in which a brain function is remarkably deteriorated like a groggy state in a process of converting from a sleep state to an awakening state immediately after awakening Sleep inertia has an influence on a sleep amount, and a sleep stage and a body temperature when awakening. It is determined that a sleep quality is good when sleep inertia is good and that a sleep quality is low when sleep inertia is bad. A good condition at sleep inertia is a condition of an appropriate sleep time, when a sleep stage immediately before awakening is in a REM sleep state, and a state in which a body temperature is risen with rise of a peripheral temperature before awakening. When sleep inertia is good, sleep inertia is weak. As a stage of NREM sleep is high, sleep inertia strongly represents, and when awakening from REM sleep, if sleep inertia is weak, a user may be easily awakened from sleep. In NREM sleep stages 1-2, sleep inertia of an intermediate stage of REM sleep and SWS is represented. Further, as a body temperature is low, there is a tendency that sleep inertia becomes serious, and as sleep time lack is serious, sleep inertia is strongly represented.

For this reason, in the present disclosure, when considering a sleep score, an appropriate sleep time and a sleep stage immediately before awakening are considered. Further, when operating a temperature adjustment device, by controlling to rise a peripheral temperature before awakening, a body temperature is controlled to rise immediately before awakening.

The sleep disturbance index SDI may be determined based on information collected by the sensor and information collected from a second electronic device other than the sensor or the user. Information collected from the sensor may include movement information, body temperature, and heartbeat information. As a movement is large, a sleep disturbance index is high. Further, when body temperature and heartbeat information deviates from a range changing in a general sleep state, it may be determined that a sleep disturbance index is high. Further, a sleep disturbance index may be input according to a user input. For example, the user may input information about a drinking state, a stamina state, and a meal time as a sleep disturbance index. Information measured by the second electronic device may be used for the sleep disturbance index. For example, when the second electronic device is a wearable device, the wearable device may collect information about the user's body temperature and heartbeat number, and the collected information may be considered for the sleep disturbance index.

The user's bio information measured through the second electronic device may be excluded from data used for determining a sleep optimal temperature in a study process. When awakening the user through the second electronic device, activation data may be collected/measured, and when such activation data are a preset threshold value or more, sleep data of a corresponding work may be excluded from the study. For example, when an exercise amount (acquired from moving distance information, and calorie consumption information) and a sleep disturbance element such as eating of food (caffeine beverage, alcohol) that may disturb sleep satisfy a preset condition, sleep data of a corresponding day may be excluded from the study. An excessive exercise causes muscle tension and awakening operation to disturb sound sleep, excessive drinking causes thirst upon sleeping to disturb sound sleep, a nicotine component of cigarette causes an awakening operation to disturb sound sleep, caffeine from a caffeinated beverage causes an awakening operation to disturb sound sleep, and thus when such a sleep disturbance element exists, collected sleep data are excluded from the study and reliability in a study process of a sleep optimal temperature can be thus improved.

For example, a reference of Table 6 may be applied.

TABLE 6

| Element | Measuring method | Condition illustration | Processing method |
|---|---|---|---|
| Exercise | Measure daily consumption calorie amount in wearable device and mobile terminal | 100 kcal or more before two hours of sleep | Exclude daily sleep evaluation score from study |
| Coffee | Direct input in mobile terminal before sleep | 4 cups or more | Exclude daily sleep evaluation score from study |
| Alcohol | Direct input in mobile terminal before sleep | When drinking | Exclude daily sleep evaluation score from study |

TABLE 6-continued

| Element | Measuring method | Condition illustration | Processing method |
|---|---|---|---|
| Health abnormality | Direct input in mobile terminal before sleep/sense (body temperature/heartbeat) with wearable device | When sick | Exclude daily sleep evaluation score from study |
| Cigarette | Direct input in mobile terminal before sleep | 12 cigarettes or more | Exclude daily sleep evaluation score from study |

In Table 6, the mobile terminal may correspond to an electronic device of the present disclosure, and the wearable device may correspond to a second electronic device.

A test temperature may be set at operation 620. The test temperature means a control temperature in random sleep. After a test temperature is determined, a temperature adjustment operation is performed based on the determined test temperature. The test temperature may be set with various methods. The test temperature may be determined according to the user's manual input. The test temperature may be determined based on a DB (information about an optimal test temperature based on a peripheral temperature, season, time, and user information) stored at the electronic device.

When a test temperature is determined at a study segment, in order to shorten a study period, the test temperature may be determined based on information such as user information (age, sex, height, weight, and sleep style). The user information may be previously stored at the electronic device. Further, a DB of a sleep optimal temperature corresponding to user information may be also stored at the electronic device or the analysis device. When starting from an optimal temperature based on user information, the study period may be shortened. For example, as user information, when a user's height n Cm and weight m Kg are input, a sleep optimal temperature corresponding to a height and weight, which are user information is acquired from the DB. A sleep optimal temperature corresponding to user information acquired from the DB may be set as a test temperature and a study process may be started.

Further, in order to shorten a study segment, by applying a plurality of sleep test temperatures at one sleep cycle, a temperature adjustment device operates and a sleep score may be acquired. At one sleep cycle, a plurality of sleep stages may generally be repeatedly represented. In an embodiment of the present disclosure, in a sleep stage repeated within one cycle, different test temperatures may be applied. By applying different test temperatures in the same sleep stage, the electronic device may control the temperature adjustment device. Thereby, at one sleep cycle, information about a plurality of test temperatures may be acquired. For example, in a first REM sleep stage of one sleep cycle, the temperature adjustment device may operate at a first test temperature, and in a second REM sleep stage, the temperature adjustment device may operate at a second test temperature.

When the temperature adjustment device operates by a test temperature, a sleep score of each test temperature is acquired at operation 630. The sleep score may be determined based on a sleep related index and user information received from the sensor. A method of acquiring a sleep score has been described in the foregoing description. After the sleep score is acquired, the acquired sleep score and related data may be stored and managed. A method of acquiring a sleep score is not limited to the foregoing method and may be acquired by combining various sleep related indexes suggested in the present disclosure.

The temperature adjustment device may determine whether acquisition of additional information is required at operation 640. The temperature adjustment device may determine whether acquisition of additional information is required based on whether the preset number of sleep score has been acquired and whether a sleep score has been acquired at a preset range of test temperature. For example, a test is performed to acquire n times of sleep scores at different temperatures, and when acquisition of n times of sleep score is complete, an additional information acquisition process may be terminated. Further, for example, when a temperature is changed by +0.x, −0.x based on a reference test temperature and when a sleep score of a range of +y to −y is acquired from a reference test temperature, and when acquisition of a preset range of sleep score is complete, an additional information acquisition process may be terminated.

Further, when a preset sleep score threshold value exists, until an acquired sleep score is equal to or greater than a preset threshold value, while changing a test temperature, sleep information of different temperatures is acquired, and when a reference temperature in which sleep information is equal to or greater than a threshold value is found, an additional information acquisition may be terminated. For example, when a threshold value of a sleep score is set to 90 point, if a sleep score acquired at a specific test temperature exceeds 90 point, a study process may be terminated, a test temperature in which 90 point as a sleep score is acquired may be determined to a user's sleep optimal temperature, and a study process may be terminated.

Figure 7:
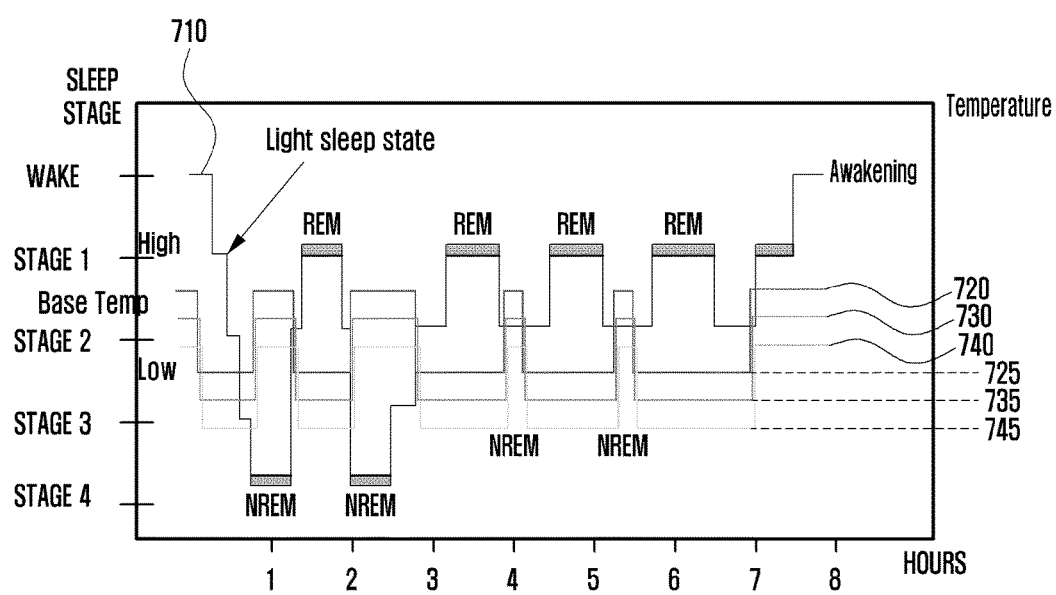
FIG. 7 is a graph illustrating an additional information acquisition process according to an embodiment of the present disclosure.

FIG. 7 is a graph illustrating an additional information acquisition process according to an embodiment of the present disclosure.

Referring to FIG. 7, a left vertical axis of a graph represents a sleep stage. In the graph, as moving from wake to a stage 4, a deep sleep state is represented. A right vertical axis of the graph represents a temperature. A horizontal axis of the graph represents an elapsed time.

710 represents a user's sleep stage. When advancing from a wake state to a sleep state based on a time axis, a user is in an awakening state, and in a process of advancing from a wake state to an awakening state, a sleep cycle of REM sleep and NREM sleep is repeated. 720 represents a temperature on a time basis when a test temperature is 725, 730 represents a temperature on a time basis when a test temperature is 735, and 740 represents a temperature on a time basis when a test temperature is 745. In an embodiment of the present disclosure, as described with reference to FIG. 7, while changing a test temperature in a study process, at various test temperatures, a user's sleep score may be acquired.

When setting a test temperature at operation 620, a sleep temperature of different three test temperatures may be compared and determined. For example, as shown in Table 7, it is assumed that a sleep score is acquired at each test temperature.

TABLE 7

|  | Test temperature | | |
|---|---|---|---|
|  | 725 | 735 | 745 |
| Sleep score | 90 | 80 | 70 |

As shown in Table 7, when a sleep score is acquired, if a test temperature moves from 735 to 725, a sleep score is high, and if a test temperature moves from 735 to 745, a sleep score is low. Therefore, when a next test temperature is set, at a temperature lower than 745, it is estimated that a lower sleep score will appear and thus at a test temperature lower than 745, a test temperature may not be set or a rate that is set to a test temperature may be lowered. Further, because it is estimated that a high sleep score will appear based on a test temperature 725, by determining a test temperature of +x and −x from the test temperature 725, a study process may be performed. When a sleep score of a test temperature of +x and −x from the test temperature 725 is lower than the test temperature 725, the test temperature 725 may be determined as an optimal temperature.

For example, an optimal temperature may be determined through data such as Table 8. In Table 8, a process of starting a test temperature from 23° C. and determining an optimal temperature to 21° C. is described.

TABLE 8

| Test temperature | 23.5 | 22.5 | 23.5 | 22.5 | 23 | 22 | 23 |
| Sleep score | 5 | 6 | 5.5 | 6 | 5.5 | 7 | 5 |
| Test temperature | 22 | 21.5 | 20.5 | 21.5 | 20.5 | 21 | 21 |
| Sleep score | 7.2 | 9 | 9.2 | 9.1 | 9.1 | 10 | 10.5 |

For example, by setting a temperature of +0.5° C. and −0.5° C. from a reference temperature 23° C. as a test temperature, a sleep score is acquired. At the same temperature, at least one time of sleep score is acquired. However, when only one time of sleep score is acquired, a sleep score may be changed according to a user's body state of the day and thus, in an embodiment of Table 8, at the same test temperature, a sleep score is acquired two times. In order to acquire a sleep score at the same test temperature, a process of acquiring a sleep score may be repeated by preset n times. As n increases, data will become more accurate, but a period that acquires an optimal temperature is extended.

As a test result of test temperatures 23.5° C. and 22.5° C., because a sleep score of 22.5° C. is higher, as a next test temperature, a sleep score of a test temperature of 23° C. and 22° C. is acquired based on 22° C. As an acquisition result of a sleep score, a sleep score of a test temperature 22° C. is higher and thus a sleep score of a test temperature of 21.5° C. and 20.5° C. is acquired based on a test temperature 21° C. Because sleep scores are similar at an upward test temperature and a downward test temperature base on 21° C., it may be estimated that an optimal temperature exists between 20.5° C. and 21.5° C. A sleep score of a test temperature 21° C. is acquired based on estimation. 21° C. that acquires a highest sleep temperature is determined as an optimal temperature.

When the preset execution number of sleep score is acquired, when a preset range of sleep score is acquired, or when a preset range of sleep score is acquired with such a method, an additional information acquisition process may be terminated.

When additional information acquisition is required with the method, the process continues at operation 620. When additional information acquisition is not required, the process continues at operation 650.

A user optimal temperature is determined at operation 650. The user optimal temperature may be determined based on a sleep score. A test temperature having a highest sleep score among sleep scores corresponding to a plurality of each test temperature may be determined as a user optimal temperature.

At a study operation, a user's optimal temperature (sleep optimal temperature, personal good sleep temperature) may be determined with such a method.

Returning again to FIG. 4, at the study control segment 430, temperature sensitivity information may be acquired. Temperature sensitivity information means individual temperature sensitivity. Individual sensitivity information may be applied in an actual sleep stage together with temperature sensitivity on a previously defined sleep stage basis. Temperature sensitivity on a sleep stage basis has been described at a basic control segment. Temperature sensitivity on a sleep stage basis may be used at the entire of the basic control segment 410, the study control segment 430, and the user specific control segment 450, but after the user's temperature sensitivity information is acquired at the study control segment 430, individual temperature sensitivity information may be applied. Even when a person having high temperature sensitivity has a small temperature change during sleep, the small temperature change may have an influence on sleep, but even when a person having low temperature sensitivity has a relatively large temperature change during sleep, the relatively large temperature change may have less influence on sleep. When individual temperature sensitivity information is acquired, a temperature change may relatively largely operate to a user having low sensitivity from an optimal temperature based on temperature sensitivity information, and by applying a relatively small temperature change to a user having high sensitivity, while minimizing an influence on sleep, the temperature adjustment system may operate with efficient power consumption.

Temperature sensitivity may be determined based on a sleep score and a test temperature of a study machine. For example, when a test temperature difference is ±T and a sleep score difference is ±P, temperature sensitivity may be obtained based on a value ±P/±T. When a sleep score difference is large, compared with a test temperature change amount, it may be determined that temperature sensitivity is high, and when a sleep score difference is small, compared with a temperature change amount, it may be determined that temperature sensitivity is low.

Figure 8:
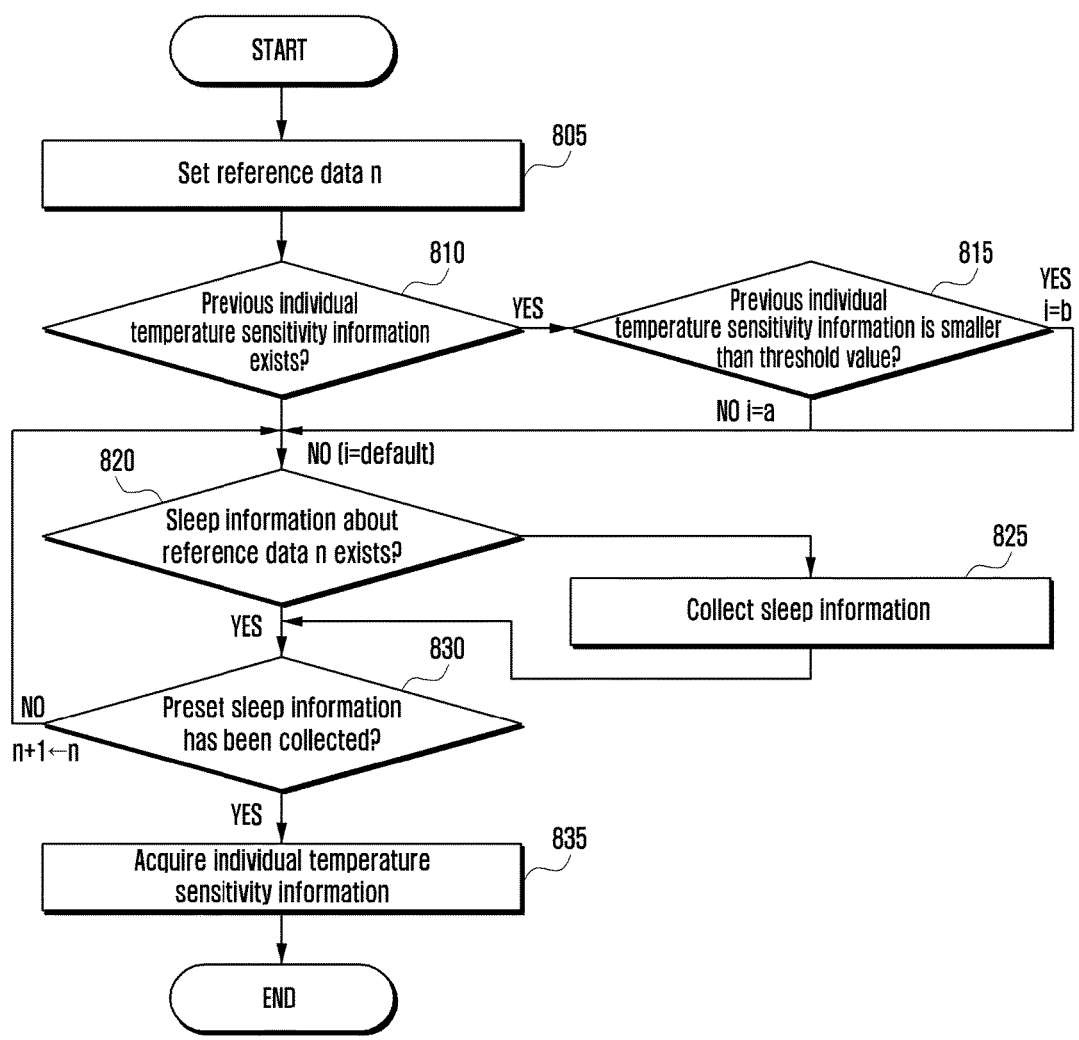
FIG. 8 is a flowchart illustrating a method of determining temperature sensitivity according to an embodiment of the present disclosure.

FIG. 8 is a flowchart illustrating a method of determining temperature sensitivity according to an embodiment of the present disclosure.

Equation 1 determines temperature sensitivity according to FIG. 8.

$$\left(\frac{1}{Wi} * \sqrt{(P1-P2)*(P1-P2)} + \right.$$

$$\frac{1}{Wi} * \sqrt{(P2-P3)*(P2-P3)} +$$

Equation 1

-continued $$\frac{1}{Wi} * \sqrt{(P3-P4)*(P3-P4)}\Bigg)\Bigg/3$$

Pn is a sleep score, and Wi is a weight value of a temperature difference. As a value of Wi, a temperature difference value may be used, and a value for compensating for distortion according to a temperature difference i may be used. When compensating for distortion according to the temperature difference i, a weight value may be previously determined. For example, a weight value according to the temperature difference i is described in Table 9.

TABLE 9

| Temperature difference i | Weight value information |
|---|---|
| 0.5 | 1.0 |
| 1.0 | 1.2 |
| 2 | 1.4 |

In Equation 1, at test temperatures of 4 times of T1, T2, T1, and T2, it is assumed that sleep scores of P1, P2, P3, and P4 are acquired. i is a temperature difference value between T1 and T2 and uses an absolute value.

Referring to FIG. 8, a reference time point or reference data n for acquiring temperature sensitivity information may be determined at operation 805. When a reference time point n is determined, temperature sensitivity may be determined using the preset data number from n-th data. In Equation 1, it has been described that four data are used, but the number of data is not limited thereto and may be smaller than or larger than four.

The temperature adjustment system determines whether individual temperature sensitivity information exists at operation 810. If individual temperature sensitivity information exists, the process continues at operation 815, and if individual temperature sensitivity information does not exist, the process continues at operation 820. A value i uses a default value at operation 820. For example, a default value may be 0.5. The temperature adjustment system determines whether previous individual temperature sensitivity information is smaller than a preset threshold value at operation 815. If previous individual temperature sensitivity information is smaller than a preset threshold value, a value i is determined to b, and if previous individual temperature sensitivity information is equal to or larger than a preset threshold value, a value i is determined to a. If temperature sensitivity information is equal to or larger than a preset threshold value, the temperature sensitivity information is relatively sensitive to a temperature and thus the temperature sensitivity information may be set to b<a. One of a or b may be the same as a default value.

The temperature adjustment system determines whether sleep information about reference data n exists at operation 820. If sleep information does not exist, the temperature adjustment system acquires sleep information as described in a study process at operation 825. After sleep information is acquired, the process continues at operation 830. If sleep information exists, the process continues at operation 830.

The temperature adjustment system determines whether the preset number of sleep information is collected at operation 830. If the preset number of sleep information is collected, the process continues at operation 835. If the preset number of sleep information is not collected, the process continues at operation 820, and the temperature adjustment system collects (n+1) information. For example, in Equation 1, the temperature adjustment system may determine whether four data are collected from a reference time point n=1. If four data are not collected, while a value n increases by 1, sleep information is collected through operation 820 or 825.

The temperature adjustment system acquires individual temperature sensitivity information based on the collected sleep information at operation 835. Individual temperature sensitivity information may use a method of Equation 1. When using a method of Equation 1, as described above, the temperature adjustment system may use a value i as a temperature difference value without using a weight value. The temperature adjustment system may acquire individual temperature sensitivity information (temperature sensitivity, temperature sensitivity information) with the method.

At a study control segment, in addition to a sleep score and temperature sensitivity, sleep information such as a personalized average hypnagogue time, a sleep amount, a wake-up time, and a sleep cycle information is studied and may be stored at a personal sleep information DB.

Returning again to FIG. 4, operation 450 of FIG. 4 is a user specific control segment (good sleep control). Operation 450 is a user specific control segment and is a segment that operates a temperature adjustment device using each user optimal temperature and/or sensitivity acquired at the study control segment. Further, user information received from the sensor may be together used.

At the user specific control segment 450, a control that guarantees good sleep and power saving is performed using information about a personal optimal temperature, individual temperature sensitivity, hypnagogue time, and sleep amount obtained through a study control. At previous operations, a personal optimal temperature and individual temperature sensitivity are not used, but at the user specific control segment 450, an optimized control for a specific user may be performed using at least one of a personal optimal temperature and individual temperature sensitivity acquired through the study control segment 430.

A sleep optimal temperature may be controlled using the acquired personal optimal temperature, and by appropriately adjusting a temperature change during sleep using temperature sensitivity information, power may be efficiently consumed.

When a user sleeps, a temperature slowly declines from a hypnagogue temperature to a personal optimal temperature for a hypnagogue estimation time, and by sensing each sleep stage, an air-conditioner operates at a setting temperature SP(n) on an operation basis. At SP(n), when n is defined to REM-0, NREM1-1, NREM2-2, NREM3-3, and NREM4-4, as n increases, SP(n) increases, and as individual temperature sensitivity increases, SP(n) reduces. When a final REM sleep stage before wake-up is estimated, a temperature slowly rises from SP(n) to Ta until a wake-up estimation time. Even at a user specific control segment, an average hypnagogue time, sleep amount, wake-up time, and sleep cycle information may be continuously stored at a personal sleep information DB. That is, even at a user specific control segment, sleep information may be continuously collected, and information such as a user's sleep information, personal optimal temperature, and individual temperature sensitivity may be updated according to collected sleep information.

Figure 9:
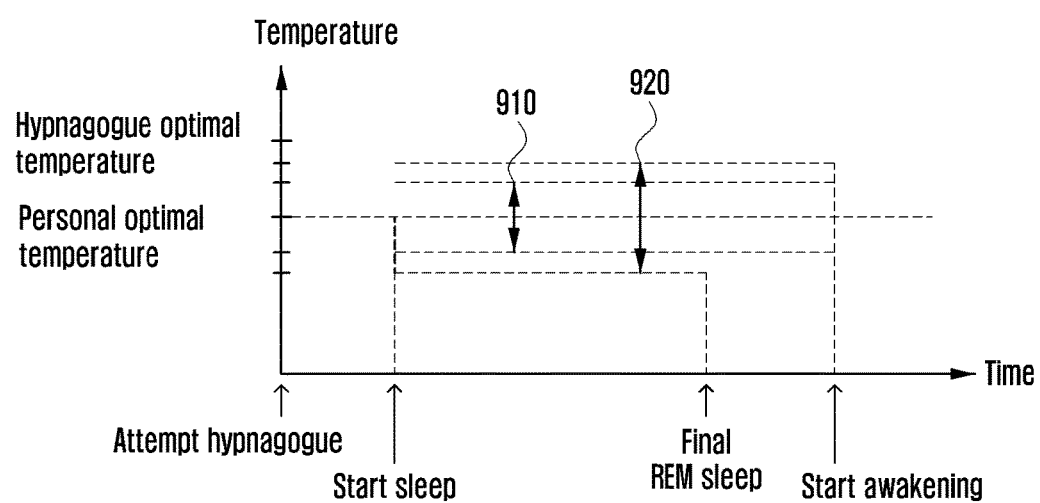
FIG. 9 is a graph illustrating a temperature adjustment process at a user specific control segment according to an embodiment of the present disclosure.

FIG. 9 is a graph illustrating a temperature adjustment process at a user specific control segment according to an embodiment of the present disclosure.

Referring to FIG. 9, the temperature adjustment device may be controlled using a personal optimal temperature acquired through the study control segment 430.

When a user sleeps, a temperature may slowly decline from a hypnagogue temperature to a personal optimal temperature for a hypnagogue estimation time. A user's hypnagogue intention may be determined by the sensor. For example, the user's movement may be determined through the sensor, and it may be determined whether the user attempts hypnagogue based on a movement level. In FIG. 9, when a hypnagogue attempt is detected, before a time point at which sleep is started, a temperature is adjusted to a personal optimal temperature.

After a temperature declines, the temperature adjustment system senses each sleep stage and operates an air-conditioner at a setting temperature SP(n) on an operation basis. At SP(n), when n is defined to REM-0, NREM1-1, NREM2-2, NREM3-3, and NREM4-4, as n increases, a difference of SP(n) from a personal optimization temperature increases and as individual temperature sensitivity increases, a difference of SP(n) from a personal optimization temperature decreases. In FIG. 9, 910 is a temperature difference threshold value when individual temperature sensitivity is high, and 920 is a temperature difference threshold value when individual temperature sensitivity is low. When individual temperature sensitivity is low, a temperature may be adjusted to a large range from a personal optimal temperature. Therefore, power may be efficiently managed according to a situation.

When a sleep stage is estimated to final REM sleep stage before wake-up, the temperature adjustment device slowly raises a temperature from SP(n) to a wake-up optimal temperature until a wake-up estimation time. A final REM sleep stage before wake-up may be detected according to a characteristic on a sleep stage basis by the sensor and may be determined by the user's sleep information collected through a study control segment. For example, after a specific time and n times of sleep cycle based on collected statistics, final REM sleep is performed and when the user's sleep information is collected, a final REM sleep time point may be determined based on such a user's statistical information.

Operation 470 is a feedback control segment. Even when operation 450 is performed, a sleep score and sleep information may be continuously collected. If a sleep score is equal to or less than a preset first threshold value, the feedback control segment is controlled to return to the study control segment 420. When returning to the study control segment 420, the temperature adjustment system controls the temperature adjustment device based on a new test temperature and may acquire a sleep score and sleep information. At a study control segment 420 of the related art, as described above, a new personal optimization temperature and individual temperature sensitivity may be acquired. When a new personal optimization temperature and individual temperature sensitivity are acquired, the process continues again at operation 450.

Further, when a sleep score is equal to or less than a preset second threshold value, by outputting a notification to the user, the temperature adjustment system operates based on the user's additional input information. It is assumed that a second threshold value has a score lower than that of a first threshold value. That is, even if the system repeatedly performs operations 430 and 450, when a sleep score declines to the second threshold value or less without enhancement, user intervention may be required. In this case, by outputting a notification to the user, the temperature adjustment system may control the user to input additional control information. The notification may use various output means such as a voice, a vibration, a display, and a light source.

As an example of an output means, a feedback user interface (UI) may be used. Various information may be input through a feedback UI. For example, the temperature adjustment system may provide an interface that determines whether a sleep temperature is hot or cold or that selects whether to set a new optimal temperature higher than a present preset optimal temperature or whether to set a new lower optimal temperature. Further, the temperature adjustment system may provide an interface to input satisfaction on a present operation temperature. Further, the temperature adjustment system may provide an interface to input relative information such as cold, cool, and slightly cool/neutral/slightly warm/warm/hot. Further, the temperature adjustment system may provide an interface to enable a user to directly input a present temperature and an optimal temperature in which the user wants. The temperature adjustment system may set a new optimal temperature based on feedback information received from the user and perform a temperature adjustment operation.

Figure 10:
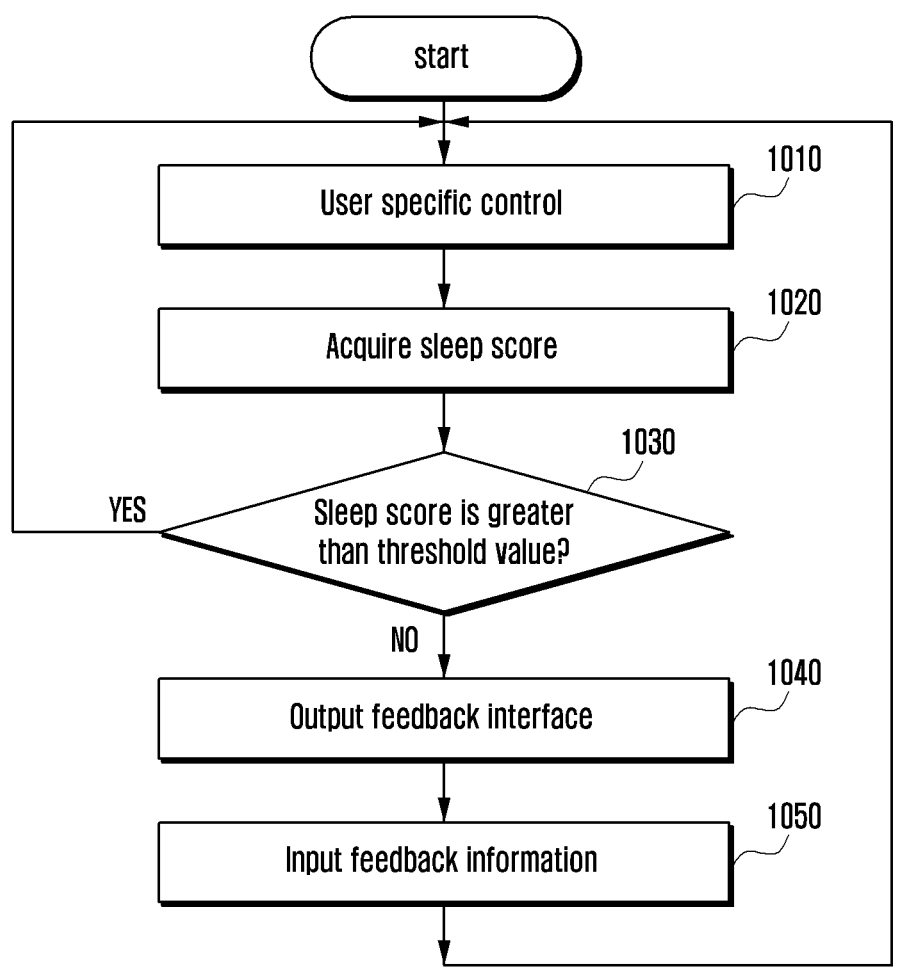
FIG. 10 is a flowchart illustrating a feedback operation according to an embodiment of the present disclosure.

FIG. 10 is a flowchart illustrating a feedback operation according to an embodiment of the present disclosure.

Referring to FIG. 10, the temperature adjustment system performs a user specific control at operation 1010. The temperature adjustment system may acquire a sleep score at operation 1020. The temperature adjustment system may compare the acquired sleep score and a preset threshold value at operation 1030. If the acquired sleep score is greater than a preset threshold value, the process returns to operation 1010, and in next sleep, a user specific control may be performed. If the acquired sleep score is equal to or smaller than a preset threshold value, the process continues at operation 1040. The temperature adjustment system may output a feedback interface at operation 1040. The feedback interface may be used for notifying to the user and may be used for receiving an input of additional information from the user.

In FIG. 10, an operation of performing at a study control segment is not described, but as described in the foregoing embodiment, the temperature adjustment system may advance and operate to a study control segment according to a threshold value reference.

The temperature adjustment system may input feedback information using a feedback interface at operation 1050. The feedback information may be an input to satisfaction in a present sleep environment, a relative expression to a present sleep temperature, and an optimal temperature in which a user targets.

The temperature adjustment system may operate at the basic control segment 410, the study control segment 430, the user specific control segment 450, and the feedback control segment 470 with the method.

Figure 11:
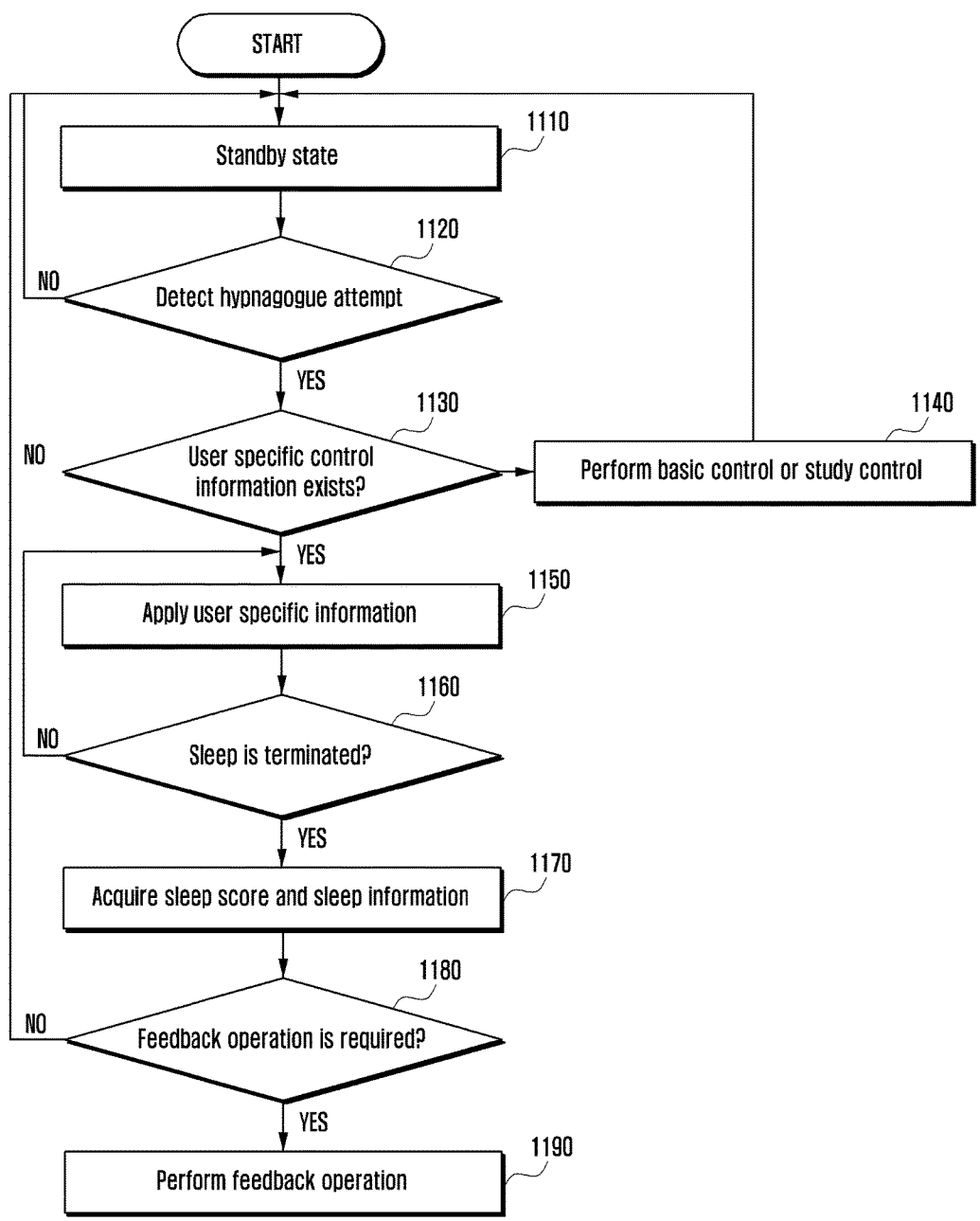
FIG. 11 is a flowchart illustrating a method of operating a temperature adjustment system according to an embodiment of the present disclosure.

FIG. 11 is a flowchart illustrating a method of operating a temperature adjustment system according to an embodiment of the present disclosure.

Referring to FIG. 11, the temperature adjustment system may be in a standby state at operation 1110. The standby state may be a time period in which the temperature adjustment system does not perform a temperature adjustment operation. Further, in a standby state, the temperature adjustment system operates, but before detecting hypnagogue, the standby state may include a case in which a temperature adjustment operation for sleep is not performed.

The temperature adjustment system may detect a hypnagogue attempt at operation 1120. The hypnagogue attempt (or sleep intention) may be determined based on a sensor. The sensor may detect a user movement to determine a hypnagogue attempt.

Figure 12:
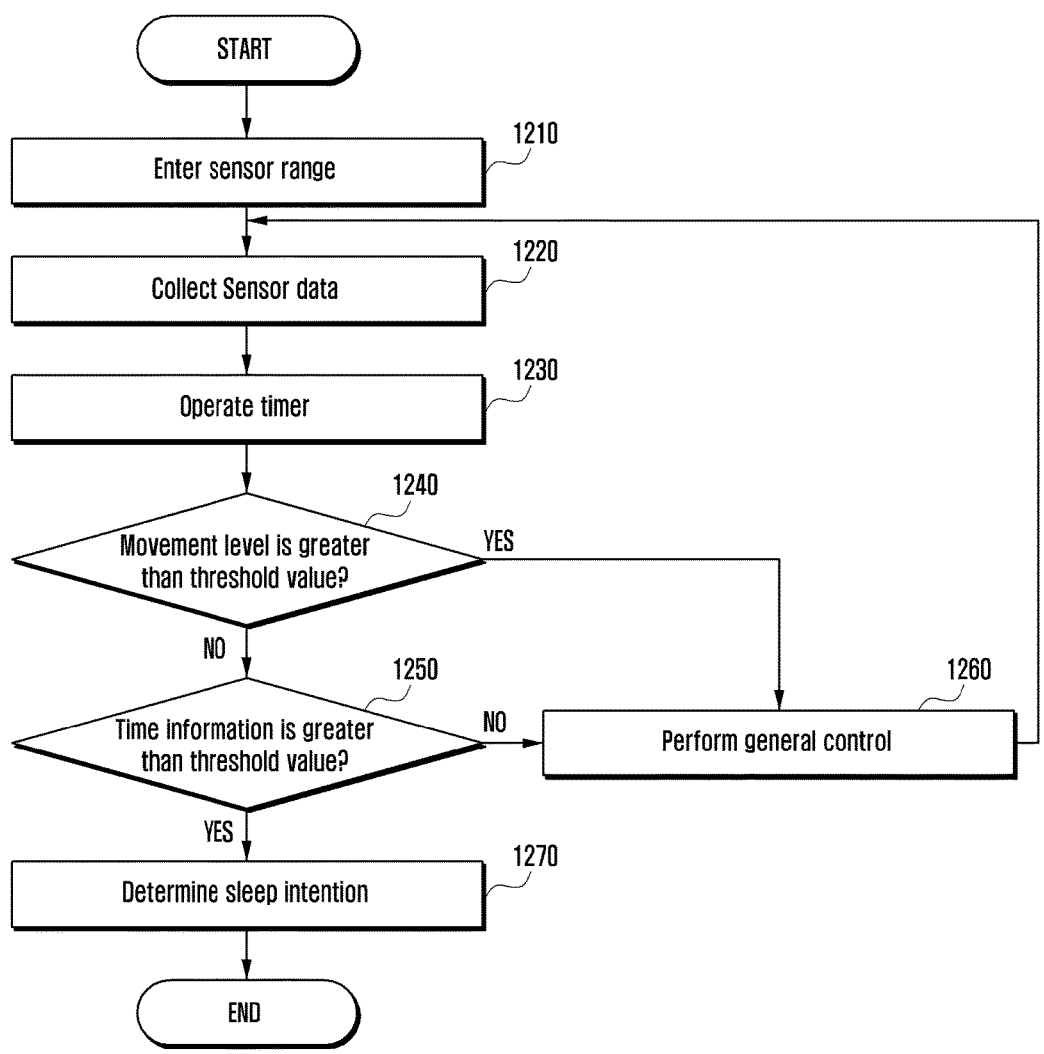
FIG. 12 is a flowchart illustrating a method of detecting a sleep intention according to an embodiment of the present disclosure.

FIG. 12 is a flowchart illustrating a method of detecting a sleep intention according to an embodiment of the present disclosure.

Referring to FIG. 12, when a user enters a sensor movement detection range at operation 1210, the sensor may detect that the user enters within a sensor range. For example, when the user approaches a bed in which the sensor is installed, the sensor may detect that the user enters within a sensor range.

A sensor of the temperature adjustment system collects data at operation 1220. The data includes data about a user movement. Further, the data may include user information (heartbeat, body temperature, and respiration) detected by the sensor.

The temperature adjustment system may drive a timer at operation 1230. The timer driving operation may be executed after operation 1240.

The temperature adjustment system may determine the user's movement level based on information collected from the sensor at operation 1240. Further, the temperature adjustment system may determine whether a user movement level is greater than a preset threshold value. In this case, a threshold value may be a threshold value for determining a sleep intention.

For example, as shown in Table 10, information about operation contents according to movement strength may be previously set.

TABLE 10

| Movement strength | Contents |
|---|---|
| Level 1 | Movement when sleeping |
| Level 2 | Movement when sleep is intended |
| Level 3 | Tossing and turning while sleeping |
| Level 4 | Movement of awakening state |

A present user's operation contents may be estimated using operation contents according to movement strength of Table 10. Contents of Table 10 are an example, movement strength may be further divided, and movement contents may be further subdivided and mapped.

The temperature adjustment system may determine a user's movement strength based on movement information acquired by the sensor. The temperature adjustment system may determine whether movement strength satisfies a preset threshold value condition using the determined movement strength. For example, because the embodiment of FIG. 12 is a level that determines a sleep intention, a threshold value may be set to a level 3. When a movement level is lower than a level 3, in a level 1 or 2, a movement may be determined as a movement during sleep or in a sleep intention. When a movement level is a level 3 or more, it may be determined that a user is in an awakening state.

The sensor may determine whether a movement level is greater than a preset threshold value at operation 1240, and if a movement level is equal to or smaller than a preset threshold value, the process continues at operation 1250. If a movement level is greater than a preset threshold value, the process continues at operation 1260. In this case, the sensor determines that a sleep intention does not exist and performs a general control. Here, a general control means a control, except for a standby mode control or a control for sleep. The process is repeated by performing operation 1220 after operation 1260.

If a movement level is equal to or less than a preset threshold value at operation 1240, by directly advancing to operation 1270 without performing operation 1250, the temperature adjustment system may determine that a sleep intention exists. However, because there is a high possibility that a movement for a very short time operates as an error, the temperature adjustment system may determine whether the movement level is maintained for a preset threshold time or more at operation 1250. For example, a movement level satisfies a threshold value condition, but if a duration time in which the movement level satisfies a threshold value condition is equal to or less than a preset threshold time, it is determined that a sleep intention does not exist. A movement level satisfies a threshold value condition and if a duration time in which the movement level satisfies a threshold value condition exceeds a preset threshold time, it is determined that a sleep intention exists.

The user's sleep intention may be determined with the method at operation 1270. The user's sleep state determination is not limited to sleep intention determination. Information about a time point at which the user enters a sleep state and a time point at which the user enters an awakening state may be acquired or determined based on movement information and a movement content mapped to the movement strength.

Returning again to FIG. 11, if a hypnagogue attempt is detected with the method of FIG. 12 or another method, the process continues at operation 1130. If a hypnagogue attempt is not detected, the process continues at operation 1110.

The temperature adjustment system may determine whether user specific control information exists at operation 1130. The user specific control information may include at least one of a personal optimal temperature or individual temperature sensitivity information. If user specific control information exists, the process continues at operation 1150. If user specific control information does not exist, the process continues at operation 1140.

The temperature adjustment system may perform a basic control or a study control at operation 1140. This has been described with reference to FIG. 4. In the basic control and the study control, temperature adjustment according to an embodiment of the present disclosure may be performed, except for a control that applies user specific control information.

When user specific information exists, by applying user specific information at operation 1150, the temperature adjustment system is controlled. For example, by applying at least one of a personal optimal temperature or individual temperature sensitivity information, the temperature adjustment system may operate.

The temperature adjustment system determines whether sleep is terminated at operation 1160. As described with reference to FIG. 12, the temperature adjustment system may determine whether sleep is terminated based on movement information. If sleep is terminated, the process continues at operation 1170, and if sleep is not terminated, the temperature adjustment system is continuously controlled at operation 1150.

If sleep is terminated, the temperature adjustment system acquires a sleep score and sleep information at a stage immediately before sleep at operation 1170. A sleep score may be calculated based on sleep information. The temperature adjustment system may determine whether a feedback operation is required based on the acquired sleep score at operation 1180. If the sleep score is equal to or greater than a preset threshold value, the temperature adjustment system does not perform a feedback operation and enters a standby state or starts a general control. If the sleep score is less than a preset threshold value, the temperature adjustment system performs a feedback operation at operation 1190. The feedback operation may include at least one of returning to a study process or outputting a feedback interface for receiving an input of user information.

Figure 13:
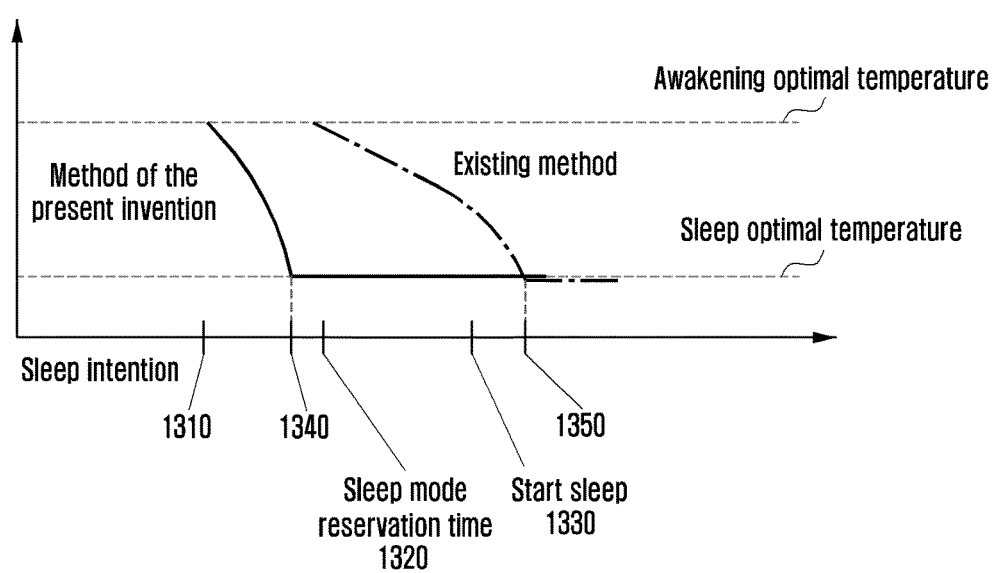
FIG. 13 is a graph illustrating a method of controlling a sleep optimal temperature arriving time according to an embodiment of the present disclosure.

FIG. 13 is a graph illustrating a method of controlling a sleep optimal temperature arriving time according to an embodiment of the present disclosure.

Referring to FIG. 13, in a method of the related art, a sleep temperature adjustment device operates without determination of the user's sleep intention. For example, a temperature adjustment device for sleep may operate according to a predetermined sleep mode time. The user's sleep intention has occurred at a time point 1310, but there is a drawback that a control for sleep operates at a preset time point 1320. Further, at hypnagogue, to lower a temperature to a sleep optimal temperature is a major element for fast hypnagogue, but because the temperature adjustment device operates late without determination of a sleep intention, at a time point 1350, which is a time later than a time point 1330 at which sleep starts, a peripheral temperature arrives at a sleep optimal temperature.

However, according to an embodiment of the present disclosure, as described with reference to FIG. 12, a user's sleep intention may be determined through a sensor, at a moment in which a sleep intention is determined, because a temperature adjustment device starts operation for sleep, a control may be performed in consideration of the user's present state. Further, immediately after a sleep intention is determined, because a temperature adjustment operation for sleep is performed, at a time point 1340, which is a time point earlier than a time point 1330, which is a sleep start time point, a peripheral temperature may arrive at a sleep optimal temperature.

In an embodiment of the present disclosure, the user's sleep information may be acquired through a study control segment. The sleep information may include information about the user's average hypnagogue time. The average hypnagogue time information is a time period from a sleep intention time point to a sleep start time point. An embodiment of the present disclosure may control a time arriving at a sleep optimal temperature using average hypnagogue time information. That is, the temperature adjustment device may be controlled such that a time arriving to a sleep optimal temperature from a sleep intention time point is smaller than an average hypnagogue time.

Figure 14:
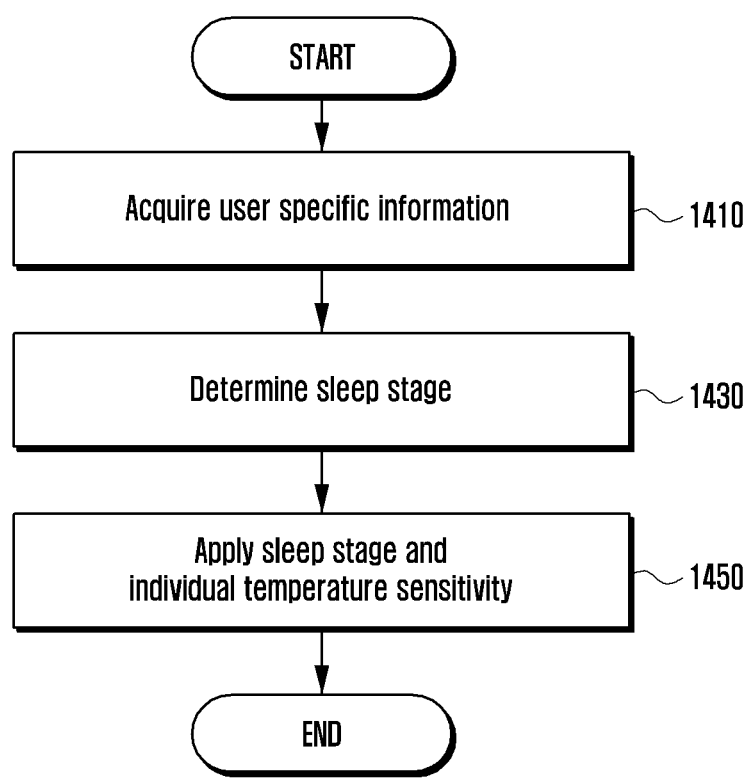
FIG. 14 is a flowchart illustrating a method of adjusting a temperature based on sensitivity according to an embodiment of the present disclosure.
Figure 15:
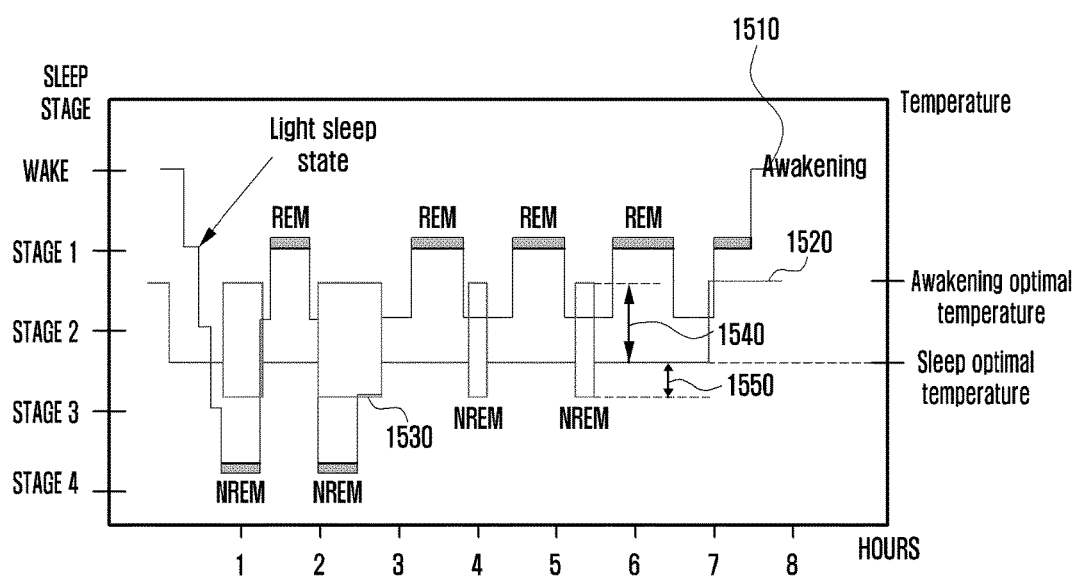
FIG. 15 is a graph illustrating temperature adjustment on a sleep stage basis based on sensitivity according to an embodiment of the present disclosure.

FIG. 14 is a flowchart illustrating a method of adjusting a temperature based on temperature sensitivity according to an embodiment of the present disclosure, and FIG. 15 is a graph illustrating temperature adjustment on a sleep stage basis based on temperature sensitivity according to an embodiment of the present disclosure.

Referring to FIG. 14, user specific information may be acquired at operation 1410. The user specific information may include a sleep optimal temperature and individual temperature sensitivity.

The temperature adjustment system may determine a sleep stage at operation 1430. The sleep stage may be divided into NREM sleep and REM sleep, and the NREM sleep may be divided into stages 1 to 4. A characteristic on each sleep stage basis has been described in the foregoing description and therefore a detailed description thereof will be omitted. The temperature adjustment system may determine a sleep stage based on user information measured by the sensor. The user information includes information about bio signal.

The temperature adjustment system may operate based on a determined sleep stage and individual temperature sensitivity at operation 1450. Because a light sleep stage such as REM sleep is sensitive to a temperature, the temperature adjustment system controls a difference between a sleep optimal temperature and a peripheral temperature to be relatively small, and at a deep sleep stage such as NREM sleep stages 3-4, by stopping operation of the temperature adjustment system or by weakly operating the temperature adjustment system, while maintaining a sleep quality, energy can be reduced. The temperature adjustment system may apply individual temperature sensitivity together with temperature adjustment on a sleep stage basis. When individual temperature sensitivity is high, a deviation from a sleep optimal temperature may be controlled not to be further large, and when individual temperature sensitivity is low, even if a deviation from a sleep optimal temperature is largely controlled, an influence on sleep quality is small.

FIG. 15 is a graph illustrating temperature adjustment on a sleep stage basis based on sensitivity according to an embodiment of the present disclosure.

Referring to FIG. 15, a left vertical axis of a graph represents a sleep stage. In the graph, as advancing from wake to a stage 4, a deep sleep state is represented. A right vertical axis of the graph represents a temperature. A horizontal axis of the graph represents an elapsed time.

1510 represents a user's sleep stage. The user advances from a wake state to a sleep state based on a time axis, becomes an awakening state, and repeats a sleep cycle of REM sleep and NREM sleep in a process of advancing from a wake state to an awakening state. 1520 represents a temperature change on a time basis when individual temperature sensitivity is low. In an REM sleep stage, which is a light sleep stage on a time zone basis, the temperature adjustment device operates at a temperature similar to a sleep optimal temperature. However, in an NREM sleep stage, which is a deep sleep stage, the temperature adjustment device may be controlled at an appropriate gap from a sleep optimal temperature. In FIG. 15, a case having a different gap on a stage basis in NREM sleep is not illustrated, but as described with reference to FIG. 5, even in an NREM sleep stage, as advancing from a stage 1 to a stage 4, a gap size may be controlled to increase. 1520 represents a case in which a peripheral temperature rises when the temperature adjustment device does not operate. When the temperature adjustment device does not operate, if a peripheral temperature declines, a temperature adjustment operation may be performed with a graph model of 1530. This is because in an NREM sleep stage, when the temperature adjustment device does not operate or weakly operates, a peripheral temperature declines.

It may be determined that a magnitude of a gap 1540 at 1520 and a magnitude of a gap 1550 at 1530 are different. This describes that individual temperature sensitivity is different. 1520 represents a case in which individual temperature sensitivity is low. Therefore, a gap from a sleep optimal temperature may be largely operated. 1530 represents a case in which individual temperature sensitivity is high. Therefore, when a gap from a sleep optimal temperature is largely operated, the user's sleep may be affected and thus in a state in which a gap from a sleep optimal temperature is relatively small, the temperature adjustment device is operated.

There may be more than one user of the temperature adjustment system. In this case, in an embodiment of the present disclosure, a reference user may be selected based on individual temperature sensitivity information. The temperature adjustment system may operate based on the reference user's user specific information. A person having high individual temperature sensitivity may be selected as a reference user based on individual temperature sensitivity. A reference user may be set based on user input information (e.g., manual setting method) instead of following individual temperature sensitivity, a user may be selected based on each user's user information (age, weight, height, and body temperature), or a user may be selected with a random selection method.

Figure 16:
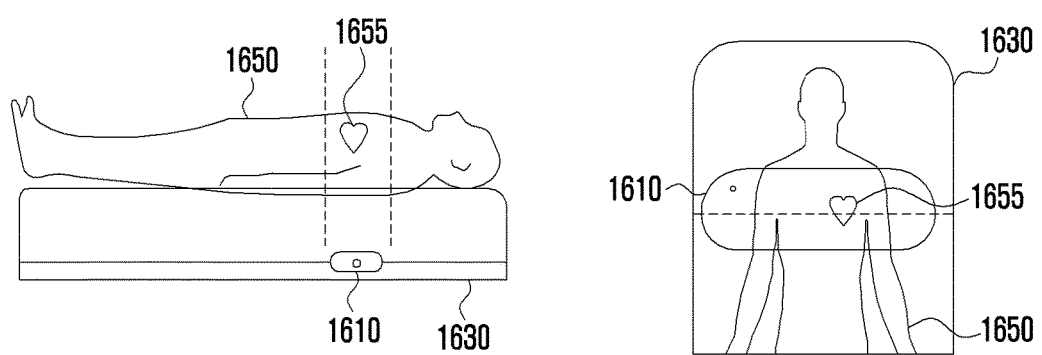
FIG. 16 is a diagram illustrating a bed pad sensor according to an embodiment of the present disclosure.

FIG. 16 is a diagram illustrating a bed pad sensor according to an embodiment of the present disclosure.

Referring to FIG. 16, the bed pad sensor may be a sleep sensor. The bed pad sensor may measure/collect the user's bio information.

A location relationship of a bed pad sensor 1610, a bed 1630, a user 1650, and a user heart 1655 will be described with reference to FIG. 16.

In FIG. 16, the bed 1630 is described as a reference, but the bed pad sensor 1610 may be attached to various objects that contact the user 1650 upon sleeping as well as the bed 1630.

The bed pad sensor 1610 may be located under a body of the user 1650. For example, when the user is in a posture that lies down on the bed 1630, as shown in FIG. 16, and the bed pad sensor 1610 may be located under the user 1650. The bed pad sensor 1610 is located under the user heart 1655 to measure the user's bio information.

The bed pad sensor 1610 may be installed within the bed 1630. Further, the bed pad sensor 1610 may be attached to the bed 1630 and may be installed at the outside of the bed. The bed pad sensor 1610 should be located within a threshold distance that can acquire bio information of the user 1650.

Figure 17A:
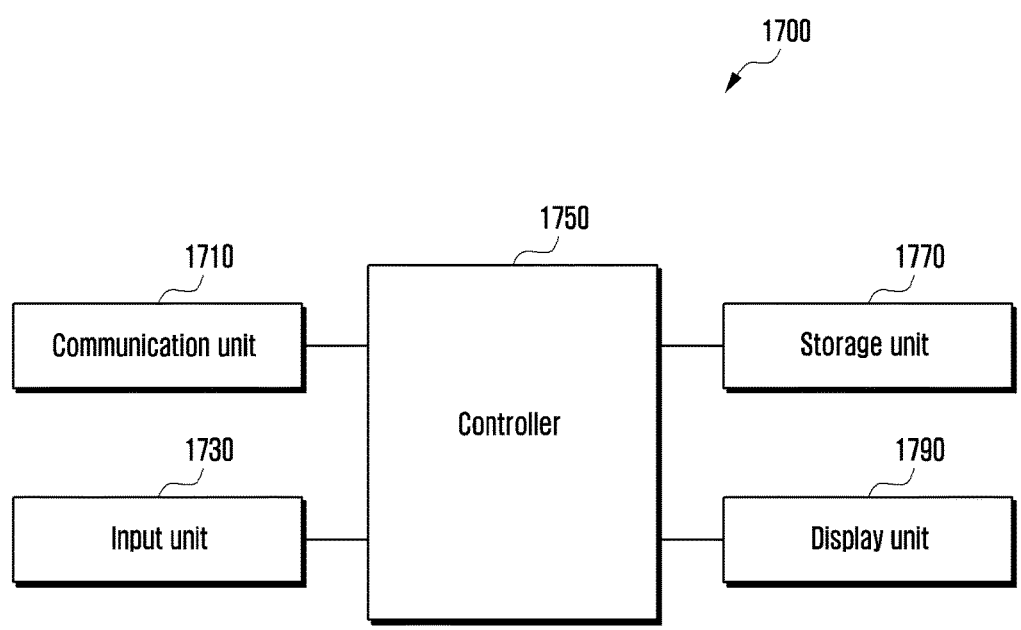
FIGS. 17A and 17B are block diagrams illustrating a configuration of an electronic device according to various embodiments of the present disclosure.

FIG. 17A is a block diagram illustrating a configuration of an electronic device according to an embodiment of the present disclosure.

Referring to FIG. 17A, an electronic device 1700 may include a communication unit 1710, an input unit 1730, a controller 1750, a storage unit 1770, and a display unit 1790. At least one of constituent elements constituting the electronic device 1700 may be omitted.

The communication unit 1710 may transmit and receive a signal to and from another network entity. In the temperature adjustment system, the communication unit 1710 may perform communication with a sensor, a cloud server, a server, a temperature adjustment device, and a second electronic device.

The communication unit 1710 transmits and receives a wireless signal to and from at least one of a base station, another web page display device, and a server on a mobile communication network. The wireless signal may include a voice call signal, audiovisual communication call signal, or various forms of data according to text/multimedia message transmission and reception. Further, the communication unit 110 may exchange data with an external device using communication technology such as wireless local area network (WLAN), Wi-Fi, ZigBee, Bluetooth, Bluetooth low energy (BLE), wireless broadband (Wibro), world interoperability for microwave access (Wimax), and high speed downlink packet access (HSDPA).

The input unit 1730 may detect a user input and transfer an input signal corresponding to the user input to the controller 1750. The input unit 1730 may include a key pad, a dome switch, a touch pad (capacitive/resistive), a jog wheel, a jog switch, a finger mouse, a wheel, etc.

The input unit 1730 may include a touch sensor, a proximity sensor, an electromagnetic sensor, a pressure sensor, etc. The input unit 1730 may detect a user's touch input or proximity input through a sensor. The input unit 1730 may be formed in an input pad in which the sensor is attached in a film form or is coupled in a panel form on a pad. For example, the input unit 1730 may be formed in an input pad of an electro magnetic resonance (EMR) or electro magnetic interference (EMI) method using an electromagnetic sensor.

The input unit 1730 may form a layer structure with the display unit 1790 to be described later to operate as an input screen. For example, the input unit 1730 may include an input pad having a touch sensor and may be formed in a touch screen panel (TSP) coupled to the display unit 1790. The input unit 130 forming a layer structure with the display unit 1790 may be referred to as a touch screen.

According to an embodiment of the present disclosure, the input unit 1730 may detect an input corresponding to a request for a web page display. Alternatively, the input unit 1730 may detect an input to a displayed web page screen.

The input unit 1730 may generate a control signal that can include information about a location, input means, and input form of a detected input and transfer the control signal to the controller 1750.

The controller 1750 may control each constituent element for general operations of the electronic device 1700.

The storage unit 1770 may store a program or instructions for the electronic device 1700. Further, at the storage unit 1770, a DB for generating a control instruction of the electronic device may be stored. The controller 1750 may perform program or instructions stored at the storage unit 1770.

The storage unit 1770 may include at least one type storage medium of a flash memory type, a hard disk type, a multimedia card micro type, a card type memory (e.g. standard definition (SD) or extreme digital (XD) memory), a random access memory (RAM), a static RAM (SRAM), a read-only memory (ROM), an electrically erasable programmable ROM (EEPROM), a Programmable ROM (PROM), a magnetic memory, a magnetic disk, and an optical disk.

The display unit 1790 displays (outputs) information processed in the electronic device 1700. For example, the display unit 1790 may display information corresponding to a presently driving application, program, or service together with a UI or a graphical UI (GUI). Further, the display unit 1790 may display feedback information and response information and may display a sleep state, a sleep score, sleep state related information, and operation information of a temperature adjustment device.

The display unit 1790 may form a mutual layer structure with the input unit 1730 to operate as a touch screen. In this case, the display unit 1790 operating as a touch screen may perform a function of an input device.

Additionally, the electronic device 1700 may further include a voice output unit, a vibration output unit, and a sensor.

According to an embodiment of the present disclosure, the controller 1750 may control to set a test temperature, to transmit a temperature adjustment instruction corresponding to the preset test temperature to a temperature adjustment device, to calculate a sleep score based on bio information received from the sensor when applying the test temperature, and to determine a sleep optimal temperature based on the calculated sleep score.

Further, according to an embodiment of the present disclosure, the controller 1750 may control to transmit a temperature adjustment instruction corresponding to a first test temperature to the temperature adjustment device, to receive first bio information measured by the sensor when applying the first test temperature, to calculate a first sleep score based on the received first bio information, to transmit a temperature adjustment instruction corresponding to a second test temperature to the temperature adjustment device, to receive second bio information measured by the sensor when applying the second test temperature, to calculate a second sleep score based on the received second bio information, and to compare the first sleep score and the second sleep score to determine a sleep optimal temperature.

Further, according to an embodiment of the present disclosure, the controller 1750 may control the communication unit 1710 to transmit and receive bio information and a temperature control instruction. Further, the controller 1750 may control to set a plurality of temperatures to a test temperature, control the temperature adjustment device to each test temperature, to acquire bio information corresponding to each test temperature, to calculate a sleep score corresponding to each test temperature based on the acquired bio information, to determine a sleep optimal temperature based on the calculated sleep score, and to transmit a control instruction for controlling the temperature adjustment device based on the sleep optimal temperature to the temperature adjustment device.

Further, the controller 1750 may control to acquire sleep stage information based on the bio information and to generate the temperature control instruction based on the sleep stage information and the sleep optimal temperature. The bio information may include at least one of blood sugar information, body temperature information, pulse information, respiration information, heartbeat information, electrocardiogram information, brainwave information, eye movement information, and movement information.

Further, the controller 1750 may control to transfer the bio information to the sleep analysis device, to receive sleep information from the sleep analysis device, and to determine the sleep optimal temperature based on the sleep information.

Further, the controller 1750 may control to acquire sleep state related information based on the bio information and to acquire the sleep score based on the sleep state related information.

Further, the controller 1750 may control to acquire a first sleep score based on acquired bio information when applying a first test temperature, to acquire a second sleep score based on acquired bio information when applying a second test temperature, and to determine the sleep optimal temperature based on the first sleep score and the second sleep score. The sleep score may be determined based on a good sleep index and a sleep disturbance index, and the good sleep index may be determined based on at least one of a hypnagogue index, sleep index, and wake-up index.

Further, the controller 1750 may control to determine temperature sensitivity based on the bio information. Temperature sensitivity may be determined based on a first sleep score of a first test temperature, a second sleep score of a second test temperature, and a temperature difference between the first test temperature and the second test temperature. In this case, the temperature control instruction may be determined based on a threshold range corresponding to the sleep optimal temperature and the temperature sensitivity.

Further, the controller 1750 may control to acquire sleep stage information and to differently apply a threshold range corresponding to temperature sensitivity on a sleep stage basis based on the sleep stage information.

Further, the controller 1750 may control to generate a control instruction that raises a peripheral temperature when detecting a final REM sleep state in entire sleep.

Further, the controller 1750 may control to acquire a sleep score of the sleep optimal temperature, to compare the sleep score with a preset threshold value, and to perform at least one of a study operation or a feedback interface output operation, if the sleep score is smaller than a preset threshold value.

In the foregoing description, a configuration of the electronic device 1700 has been described. However, in the present disclosure, a configuration of the electronic device 1700 is not limited to that of FIG. 17A. In an embodiment of the present disclosure, the electronic device 1700 may perform an operation and a function for an embodiment of the present disclosure described with reference to FIGS. 2A to 2E, 3A, 3B, and 4 to 16. Further, the electronic device 1700 may be connected to a sensor, analysis device, and temperature adjustment device by wire and wireless and may further include at least one of the sensor, analysis device, and temperature adjustment device.

Figure 17B:
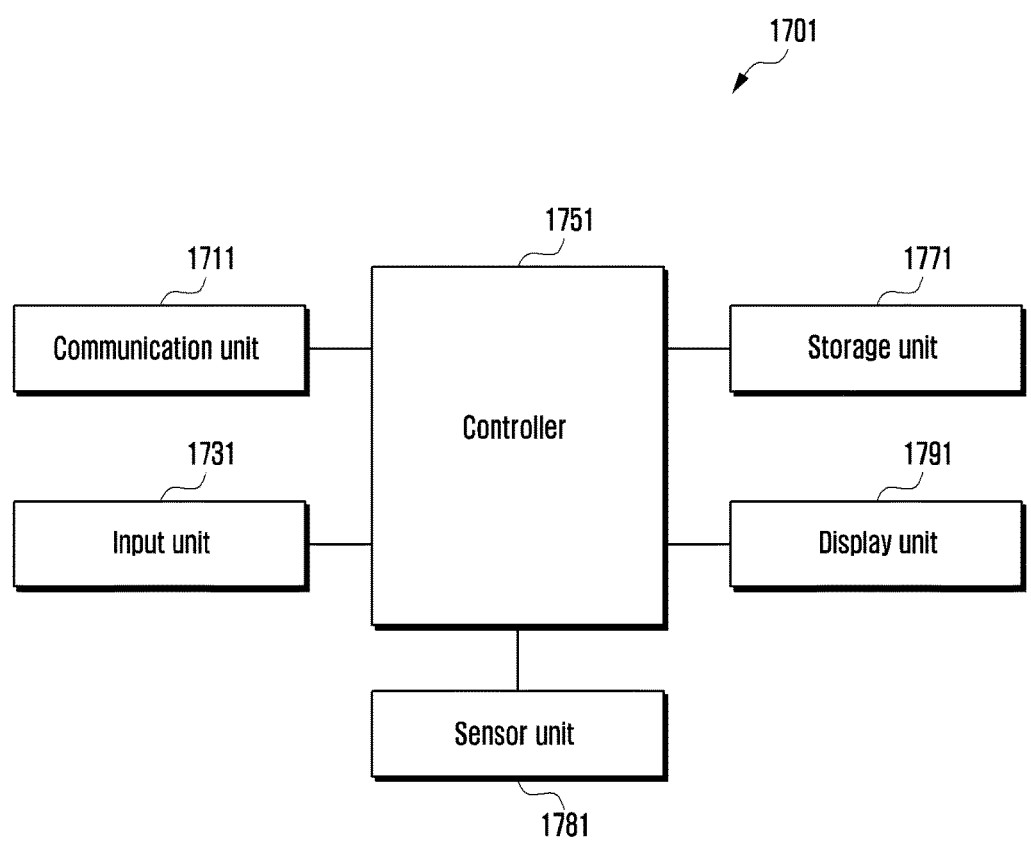

FIG. 17B is a block diagram illustrating a configuration of an electronic device according to an embodiment of the present disclosure.

Referring to FIG. 17B, an electronic device 1701 may include a communication unit 1711, an input unit 1731, a controller 1751, a storage unit 1771, a sensor unit 1781, and a display unit 1791. At least one of constituent elements constituting the electronic device 1701 may be omitted.

Compared with FIG. 17A, the electronic device 1701 of FIG. 17B includes a sensor unit 1781. The sensor unit 1781 may include at least one of, for example, a gesture sensor, a gyro sensor, an atmospheric pressure sensor, a magnetic sensor, an acceleration sensor, a grip sensor, a proximity sensor, a color sensor, a bio sensor, a temperature/humidity sensor, an intensity of illumination sensor, or an ultra violet (UV) sensor, an eyeball sensor, a pulse sensor, a heartbeat sensor, and a brainwave sensor.

In an embodiment of the present disclosure, the sensor unit 1781 may be a sensor that detects a user's bio signal (bio information). The bio information may be at least one of the user's blood sugar information, body temperature information, pulse information, respiration information, heartbeat information, electrocardiogram information, brainwave information, eye movement information (movement of eyeball, blink, the number of blink, movement of eyelid, and tear), and movement information.

Further, the sensor unit 1781 may detect a peripheral temperature. When the sensor unit 1781 directly measures a peripheral temperature, the electronic device 1701 may directly control operation of a temperature adjustment device. For example, the electronic device 1701 may directly adjust on/off, intensity, and time. That is, when wanting to operate to a specific temperature n, the electronic device 1701 may directly measure a peripheral temperature based on a directly measured temperature and transmit an on/off instruction for operating to the specific temperature n to the temperature adjustment device.

When a temperature sensor for measuring a peripheral temperature is located at a specific location or an electronic device for temperature adjustment, a temperature of the specific location can be more accurately controlled and user satisfaction can be maximized.

A configuration, operation, and function of each unit of FIG. 17B, except for the sensor unit 1781 correspond to those of each unit of FIG. 17A and therefore a detailed description thereof is omitted.

Figure 18:
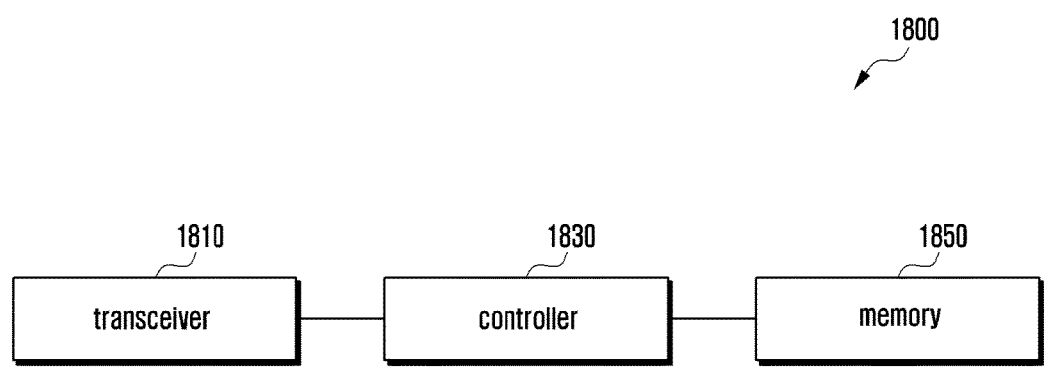
FIG. 18 is a block diagram illustrating a configuration of an analysis device according to an embodiment of the present disclosure.

FIG. 18 is a block diagram illustrating a configuration of an analysis device according to an embodiment of the present disclosure.

Referring to FIG. 18, an analysis device 1800 may include a communication unit (e.g., transceiver) 1810 that transmits and receives a signal, a controller 1830 that controls general operations of the analysis device 1800, and a storage unit (e.g., memory) 1850 that stores a DB for sleep analysis. The controller 1830 of the analysis device 1800 may control to receive user information from an electronic device and to analyze sleep information based on user information. Further, the controller 1830 may transmit the sleep information to the electronic device.

In the foregoing description, a configuration of the analysis device 1800 has been described. However in the present disclosure, a configuration and operation of the analysis device are not limited to those of FIG. 18. In an embodiment of the present disclosure, the analysis device 1800 may perform an operation of an embodiment of the present disclosure described with reference to FIGS. 2A to 2E, 3A, 3B, and 4 to 16.

Figure 19:
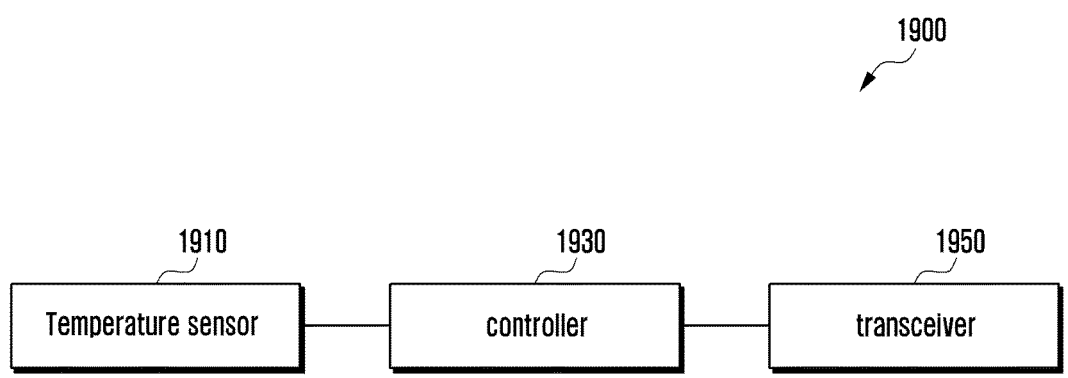
FIG. 19 is a block diagram illustrating a configuration of a temperature adjustment device according to an embodiment of the present disclosure.

FIG. 19 is a block diagram illustrating a configuration of a temperature adjustment device according to an embodiment of the present disclosure.

Referring to FIG. 19, a temperature adjustment device 1900 may include a communication unit (e.g., transceiver) 1950 that transmits and receives a signal, a controller 1930 that controls general operations of the temperature adjustment device 1900, and a temperature sensor 1910. The controller 1930 may control the temperature adjustment device 1900 based on a control message received from an electronic device. According to an embodiment of the present disclosure, the control message is generated based on user information measured by a sensor, and a temperature may be adjusted based on user specific information using the control message.

In an embodiment of the present disclosure, the electronic device 1700 of FIG. 17A may be included in the temperature adjustment device 1900. That is, instead of a method in which the electronic device 1700 transmits a control message to the temperature adjustment device 1900, the temperature adjustment device 1900 may receive user information from the sensor and exchange sleep information with an analysis device to directly control operation thereof. In this case, the controller 1930 of the temperature adjustment device 1900 may perform an operation of the electronic device 1700 of FIG. 17A. Further, the sensor or the analysis device may be included in the temperature adjustment device 1900.

In the foregoing description, a configuration of the temperature adjustment device 1900 has been described. However in the present disclosure, a configuration and operation of the temperature adjustment device are not limited to those of FIG. 19. In an embodiment of the present disclosure, the temperature adjustment device 1900 may perform an operation of an embodiment of the present disclosure described with reference to FIGS. 2A to 2E, 3A, 3B, and 4 to 16.

As described above, according to an embodiment of the present disclosure, a device and method for adjusting a temperature can be provided.

Further, according to an embodiment of the present disclosure, for a comfortable sleep environment, a method and apparatus for controlling a temperature adjustment device based on a sensing device can be provided.

Further, according to an embodiment of the present disclosure, a method and apparatus for providing a sleep environment appropriate to each user by using an individual good sleep temperature and temperature sensitivity using a good sleep index and efficiently managing power can be provided.

While the present disclosure has been shown and described with reference to various embodiments thereof, it will be understood by those skilled in the art that various changes in form and details may be made therein without departing from the spirit and scope of the present disclosure as defined by the appended claims and their equivalents.

What is claimed is:

1. An electronic device for receiving user information from a sensor, the electronic device comprising:
a transceiver configured to transmit a temperature control instruction to a temperature adjustment device; and
at least one processor configured to:
control the transceiver to transmit a first temperature control instruction to the temperature adjustment device such that the temperature adjustment device operates to maintain a first temperature,
calculate a sleep score based on the user information received from the sensor when applying the first temperature, and
determine a sleep optimal temperature based on the calculated sleep score,
wherein the at least one processor is further configured to:
determine temperature sensitivity based on the user information,
determine threshold range at the sleep optimal temperature based on the temperature sensitivity and the sleep optimal temperature, and
control the transceiver to transmit a second temperature control instruction to the temperature adjustment device such that the temperature adjustment device operates within the threshold range of the temperature.

2. The electronic device of claim 1, wherein the at least one processor is further configured to transmit a temperature control instruction for controlling the temperature adjustment device to the temperature adjustment device based on the sleep optimal temperature.

3. The electronic device of claim 1, wherein the at least one processor is further configured to:
acquire sleep stage information based on the user information, and
generate a temperature control instruction based on the sleep stage information and the sleep optimal temperature.

4. The electronic device of claim 1, wherein the user information comprises at least one of blood sugar information, body temperature information, pulse information, respiration information, heartbeat information, electrocardiogram information, brainwave information, eye movement information, or movement information.

5. The electronic device of claim 1, wherein the at least one processor is further configured to:
transfer the user information to a sleep analysis device,
receive sleep information from the sleep analysis device, and
determine the sleep optimal temperature based on the sleep information.

6. The electronic device of claim 1, wherein the at least one processor is further configured to:
acquire sleep state related information based on the user information, and
acquire the sleep score based on the sleep state related information.

7. The electronic device of claim 1, wherein the at least one processor is further configured to:
acquire a first sleep score based on acquired user information when applying a first test temperature,
acquire a second sleep score based on acquired user information when applying a second test temperature, and
determine the sleep optimal temperature based on the first sleep score and the second sleep score.

8. The electronic device of claim 1,
wherein the sleep score is determined based on a good sleep index and a sleep disturbance index, and
wherein the good sleep index is determined based on of at least one of a hypnagogue index, a sleep index, or a wake-up index.

9. The electronic device of claim 1, wherein the temperature sensitivity is determined based on a first sleep score of a first test temperature, a second sleep score of a second test temperature, and a temperature difference between the first test temperature and the second test temperature.

10. The electronic device of claim 1, wherein the at least one processor is further configured to:
acquire sleep stage information, and
generate a temperature control instruction to which the threshold range, corresponding to the temperature sensitivity on a sleep stage basis, is applied based on the sleep stage information.

11. The electronic device of claim 1, wherein the at least one processor is further configured to generate a control instruction that raises a peripheral temperature when detecting a final rapid eye movement (REM) sleep state in an entire sleep.

12. The electronic device of claim 1, wherein the at least one processor is further configured to:
acquire a third sleep score of the sleep optimal temperature,
compare the third sleep score with a preset threshold value, and
perform at least one of a study operation or a feedback interface output operation, if the third sleep score is smaller than a preset threshold value.

13. A method of controlling an electronic device for receiving user information from a sensor, the method comprising:
transmitting, by a transceiver, a first temperature control instruction to a temperature adjustment device such that the temperature adjustment device operates to maintain a first temperature;
calculating, by the at least one processor, a sleep score based on the user information received from the sensor when applying the test temperature; and
determining, by the at least one processor, a sleep optimal temperature based on the calculated sleep score,
wherein the method is further comprising:
determining, by the at least one processor, temperature sensitivity based on the user information;
determining, by the at least one processor, threshold range at the sleep optimal temperature based on the temperature sensitivity and the sleep optimal temperature; and
transmitting, by the at least one processor, a second temperature control instruction to the temperature adjustment device such that the temperature adjustment device operates within the threshold range of the temperature.

14. The method of claim 13, further comprising transmitting a temperature control instruction for controlling the temperature adjustment device to the temperature adjustment device based on the sleep optimal temperature.

15. The method of claim 13, further comprising:
acquiring sleep stage information based on the user information,
wherein a temperature control instruction is generated based on the sleep stage information and the sleep optimal temperature.

16. The method of claim 13, wherein the user information comprises at least one of blood sugar information, body temperature information, pulse information, respiration information, heartbeat information, electrocardiogram information, brainwave information, eye movement information, or movement information.

* * * * *